United States Patent
Zacharchuk et al.

(10) Patent No.: US 9,265,784 B2
(45) Date of Patent: *Feb. 23, 2016

(54) ANTINEOPLASTIC COMBINATIONS OF 4-ANILINO-3-CYANOQUINOLINES AND CAPECITABINE

(71) Applicant: WYETH LLC, New York, NY (US)

(72) Inventors: Charles Michael Zacharchuk, Westford, MA (US); Susan Elizabeth Quinn, Norwood, MA (US); Kenneth Kuan-Yuen Wang, Waltham, MA (US); Florence Marie Helene Binlich, Ville d'Avray (FR)

(73) Assignee: WYETH LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/169,015

(22) Filed: Jan. 30, 2014

(65) Prior Publication Data

US 2014/0171384 A1 Jun. 19, 2014

Related U.S. Application Data

(63) Continuation of application No. 12/534,895, filed on Aug. 4, 2009, now Pat. No. 8,669,273.

(60) Provisional application No. 61/172,466, filed on Apr. 24, 2009, provisional application No. 61/085,913, filed on Aug. 4, 2008.

(51) Int. Cl.
  *A61K 31/517* (2006.01)
  *A61K 31/7068* (2006.01)
  *A61K 45/06* (2006.01)
  *A61K 31/4709* (2006.01)
  *A61K 31/496* (2006.01)

(52) U.S. Cl.
  CPC ......... *A61K 31/7068* (2013.01); *A61K 31/4709* (2013.01); *A61K 31/496* (2013.01); *A61K 31/517* (2013.01); *A61K 45/06* (2013.01)

(58) Field of Classification Search
  CPC combination set(s) only.
  See application file for complete search history.

(56) References Cited

U.S. PATENT DOCUMENTS

| | | |
|---|---|---|
| 4,966,891 A | 10/1990 | Fujiu et al. |
| 5,453,497 A | 9/1995 | Kamiya et al. |
| 5,472,949 A | 12/1995 | Arasaki et al. |
| 5,476,932 A | 12/1995 | Brinkman et al. |
| 5,760,041 A | 6/1998 | Wissner et al. |
| 6,002,008 A | 12/1999 | Wissner et al. |
| 6,143,764 A | 11/2000 | Kubo et al. |
| 6,251,912 B1 | 6/2001 | Wissner et al. |
| 6,288,082 B1 | 9/2001 | Wissner et al. |
| 6,297,258 B1 | 10/2001 | Wissner et al. |
| 6,384,051 B1 | 5/2002 | Frost et al. |
| 6,387,371 B1 | 5/2002 | Hudziak et al. |
| 6,399,063 B1 | 6/2002 | Hudziak et al. |
| 6,432,979 B1 | 8/2002 | Frost et al. |
| 6,511,986 B2 | 1/2003 | Zhang et al. |
| 6,617,333 B2 | 9/2003 | Rabindran et al. |
| 6,780,996 B2 | 8/2004 | Boschelli et al. |
| 6,821,515 B1 | 11/2004 | Cleland et al. |
| 6,821,988 B2 | 11/2004 | Wissner et al. |
| 7,126,025 B2 | 10/2006 | Considine et al. |
| 7,189,735 B2 | 3/2007 | Dukart et al. |
| 7,294,468 B2 | 11/2007 | Bell et al. |
| 7,297,795 B2 | 11/2007 | Sutherland et al. |
| 7,306,801 B2 | 12/2007 | Caligiuri et al. |
| RE40,418 E | 7/2008 | Rabindran et al. |
| 7,399,865 B2 | 7/2008 | Wissner et al. |
| 7,846,936 B2 | 12/2010 | Hilberg et al. |
| 7,897,159 B2 | 3/2011 | Weber |
| 7,915,402 B2 | 3/2011 | Anderson et al. |
| 7,982,043 B2 | 7/2011 | Wissner et al. |
| 8,022,216 B2 | 9/2011 | Lu et al. |
| 8,173,814 B2 | 5/2012 | Lu et al. |
| 8,338,456 B2 | 12/2012 | Coughlin et al. |
| 8,394,959 B2 | 3/2013 | Lu et al. |
| 8,518,446 B2 | 8/2013 | Ashraf et al. |
| 8,524,281 B2 | 9/2013 | Venkata Ramana Rao et al. |
| 8,669,273 B2 * | 3/2014 | Zacharchuk et al. ......... 514/312 |
| 8,790,708 B2 | 7/2014 | Ashraf et al. |
| 2002/0183239 A1 | 12/2002 | Gibbons, Jr. et al. |
| 2002/0183240 A1 | 12/2002 | Gibbons et al. |
| 2002/0198137 A1 | 12/2002 | Dukart et al. |
| 2003/0149056 A1 | 8/2003 | Wissner et al. |
| 2003/0153593 A1 | 8/2003 | Dukart et al. |

(Continued)

FOREIGN PATENT DOCUMENTS

| | | |
|---|---|---|
| EP | 0693285 A2 | 1/1996 |
| EP | 1448531 B1 | 8/2007 |

(Continued)

OTHER PUBLICATIONS

Wong, K-K. Clin. Cancer Res., Aug. 1, 2007, vol. 13 (15 Suppl), pp. 4593s-4596s.*
Wissner et al. Arch. Pharm. Chem. Life Sci., 2008, vol. 341, pp. 465-477.*
Minami et al. Oncogene, 2007, vol. 26, pp. 5023-5027.*
Al-Muhammed et al., "In-vivo studies on dexamethasone sodium phosphate liposomes," J. Microencapsul., 13:293-306 (1996).

(Continued)

Primary Examiner — James D Anderson
(74) Attorney, Agent, or Firm — Jones Day

(57) ABSTRACT

A combination of a 4-anilino-3-cyanoquinoline compound (e.g. HKI-272, SKI-606, EKB-569) and a capecitabine compound in the treatment of a neoplasm is provided. Regimens, kits, and methods for treatment of neoplasm, including breast cancer including metastatic breast cancer, and lung cancer, using this combination, optionally in combination with other anti-neoplastic agents, or immune modulators are also described.

23 Claims, No Drawings

(56) References Cited

U.S. PATENT DOCUMENTS

| | | |
|---|---|---|
| 2004/0162442 A1 | 8/2004 | Considine et al. |
| 2004/0176339 A1 | 9/2004 | Sherman et al. |
| 2004/0209930 A1 | 10/2004 | Carboni et al. |
| 2004/0258662 A1 | 12/2004 | Gibbons et al. |
| 2005/0025825 A1 | 2/2005 | Heasley et al. |
| 2005/0043233 A1 | 2/2005 | Stefanic et al. |
| 2005/0059678 A1 | 3/2005 | Wissner et al. |
| 2005/0129761 A1 | 6/2005 | Venkata Ramana Rao et al. |
| 2005/0136063 A1 | 6/2005 | Wang et al. |
| 2005/0187184 A1 | 8/2005 | Gibbons, Jr. et al. |
| 2005/0272758 A1 | 12/2005 | Bayever et al. |
| 2006/0030547 A1 | 2/2006 | Dukart et al. |
| 2006/0035904 A1 | 2/2006 | Gibbons et al. |
| 2006/0058311 A1 | 3/2006 | Munzert et al. |
| 2006/0079515 A1 | 4/2006 | Frost |
| 2006/0128793 A1 | 6/2006 | Zask et al. |
| 2006/0178387 A1 | 8/2006 | Fujimoto-Ouchi et al. |
| 2006/0235046 A1 | 10/2006 | Zacharchuk et al. |
| 2006/0270668 A1 | 11/2006 | Chew et al. |
| 2006/0270669 A1 | 11/2006 | Chew et al. |
| 2007/0014859 A1 | 1/2007 | Shah et al. |
| 2007/0104721 A1 | 5/2007 | Moore et al. |
| 2007/0105887 A1 | 5/2007 | Moore |
| 2007/0281932 A1 | 12/2007 | Bernier et al. |
| 2008/0112888 A1 | 5/2008 | Wang |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0286771 A1 | 11/2008 | Hudson et al. |
| 2008/0286785 A1 | 11/2008 | Nishio et al. |
| 2009/0035269 A1 | 2/2009 | Weber |
| 2009/0047278 A1 | 2/2009 | Owa et al. |
| 2009/0060873 A1 | 3/2009 | Sporn et al. |
| 2009/0176827 A1 | 7/2009 | Lu et al. |
| 2009/0246198 A1 | 10/2009 | Dong et al. |
| 2009/0297519 A1 | 12/2009 | Moore et al. |
| 2009/0306101 A1 | 12/2009 | Solca et al. |
| 2009/0312360 A1 | 12/2009 | Zacharchuk |
| 2009/0317456 A1 | 12/2009 | Karrasch et al. |
| 2009/0318480 A1 | 12/2009 | Solca |
| 2009/0325877 A1 | 12/2009 | Grunt et al. |
| 2010/0041904 A1 | 2/2010 | Jiang et al. |
| 2010/0048540 A1 | 2/2010 | Boyle et al. |
| 2010/0048892 A1 | 2/2010 | Anderson et al. |
| 2010/0056777 A1 | 3/2010 | Anderson et al. |
| 2010/0069340 A1 | 3/2010 | Zacharchuk et al. |
| 2010/0081632 A1 | 4/2010 | Oksenberg et al. |
| 2010/0087482 A1 | 4/2010 | Haber et al. |
| 2010/0092490 A1 | 4/2010 | Uenaka et al. |
| 2010/0105031 A1 | 4/2010 | Matsui et al. |
| 2010/0113474 A1 | 5/2010 | Zacharhuk et al. |
| 2010/0120072 A1 | 5/2010 | Lorence et al. |
| 2010/0120768 A1 | 5/2010 | Steinberg et al. |
| 2010/0143340 A1 | 6/2010 | Kolhe et al. |
| 2010/0143350 A1 | 6/2010 | Green et al. |
| 2010/0166744 A1 | 7/2010 | Wong |
| 2010/0189773 A1 | 7/2010 | Mortimore et al. |
| 2010/0297118 A1 | 11/2010 | Macdougall et al. |
| 2010/0298760 A1 | 11/2010 | Olle et al. |
| 2010/0310503 A1 | 12/2010 | Li et al. |
| 2011/0014117 A1 | 1/2011 | Wang et al. |
| 2011/0045459 A1 | 2/2011 | Mischel et al. |
| 2011/0052570 A1 | 3/2011 | Klagsbrun et al. |
| 2011/0091421 A1 | 4/2011 | Mann |
| 2011/0091524 A1 | 4/2011 | Wang et al. |
| 2011/0097340 A1 | 4/2011 | Ramachandra et al. |
| 2011/0104256 A1 | 5/2011 | Wang et al. |
| 2011/0111018 A1 | 5/2011 | Ashraf et al. |
| 2011/0129456 A1 | 6/2011 | Wang et al. |
| 2011/0165257 A1 | 7/2011 | Rao et al. |
| 2012/0270896 A1 | 10/2012 | Zacharchuk |
| 2012/0308560 A1 | 12/2012 | Moore et al. |
| 2013/0189274 A1 | 7/2013 | Berkenblit et al. |
| 2013/0281488 A1 | 10/2013 | Lu et al. |
| 2014/0004203 A1 | 1/2014 | Rao et al. |
| 2014/0050721 A1 | 2/2014 | Moore et al. |
| 2014/0171384 A1 | 6/2014 | Zacharchuk et al. |

FOREIGN PATENT DOCUMENTS

| | | |
|---|---|---|
| EP | 1663978 B1 | 11/2007 |
| EP | 1848414 B1 | 4/2011 |
| JP | 2003-519698 A | 6/2003 |
| WO | WO 92/22653 A1 | 12/1992 |
| WO | 96/33978 | 10/1996 |
| WO | 96/33980 | 10/1996 |
| WO | WO 98/43960 A1 | 10/1998 |
| WO | WO 00/18761 A1 | 4/2000 |
| WO | WO 02/080975 A1 | 10/2002 |
| WO | WO 02/098416 A2 | 12/2002 |
| WO | WO 03/050090 A1 | 6/2003 |
| WO | WO 03/103676 A2 | 12/2003 |
| WO | WO 2004/004644 A2 | 1/2004 |
| WO | WO 2004/066919 A2 | 8/2004 |
| WO | WO 2004/078133 A2 | 9/2004 |
| WO | WO 2004/093854 A2 | 11/2004 |
| WO | 2005/018677 A2 | 3/2005 |
| WO | WO 2005/032513 A2 | 4/2005 |
| WO | WO 2005/034955 A1 | 4/2005 |
| WO | WO 2005/037287 A1 | 4/2005 |
| WO | WO 2005/044091 A2 | 5/2005 |
| WO | WO 2005/087265 A1 | 9/2005 |
| WO | WO 2005/094357 A2 | 10/2005 |
| WO | WO 2006/044453 A1 | 4/2006 |
| WO | WO 2006/044748 A2 | 4/2006 |
| WO | 2006/081985 A1 | 8/2006 |
| WO | WO 2006/084058 A2 | 8/2006 |
| WO | WO 2006/095185 A1 | 9/2006 |
| WO | WO 2006/098978 A1 | 9/2006 |
| WO | 2006/113151 A2 | 10/2006 |
| WO | WO 2006/113151 A2 | 10/2006 |
| WO | 2006/120557 A1 | 11/2006 |
| WO | WO 2006/116514 A2 | 11/2006 |
| WO | WO 2006/120573 A2 | 11/2006 |
| WO | WO 2006/127205 A2 | 11/2006 |
| WO | WO 2006/127207 A1 | 11/2006 |
| WO | WO 2007/000234 A1 | 1/2007 |
| WO | WO 2007/011619 A2 | 1/2007 |
| WO | 2007/056118 A1 | 5/2007 |
| WO | WO 2007/075794 A2 | 7/2007 |
| WO | WO 2007/095038 A2 | 8/2007 |
| WO | WO 2007/130438 A2 | 11/2007 |
| WO | WO 2007/137187 A2 | 11/2007 |
| WO | WO 2007/139797 A2 | 12/2007 |
| WO | 2008/076143 A1 | 6/2008 |
| WO | WO 2008/076278 A2 | 6/2008 |
| WO | WO 2008/089087 A2 | 7/2008 |
| WO | WO 2008/093878 A1 | 8/2008 |
| WO | WO 2008/121467 A2 | 10/2008 |
| WO | WO 2008/127710 A2 | 10/2008 |
| WO | WO 2008/130910 A1 | 10/2008 |
| WO | 2009/042613 A1 | 4/2009 |
| WO | WO 2009/052264 A2 | 4/2009 |
| WO | WO 2009/061349 A1 | 5/2009 |
| WO | WO 2009/105234 A2 | 8/2009 |
| WO | WO 2009/108637 A1 | 9/2009 |
| WO | WO 2009/111073 A2 | 9/2009 |
| WO | WO 2009/121031 A2 | 10/2009 |
| WO | WO 2009/126662 A1 | 10/2009 |
| WO | WO 2009/129545 A1 | 10/2009 |
| WO | WO 2009/129546 A1 | 10/2009 |
| WO | WO 2009/129548 A1 | 10/2009 |
| WO | WO 2009/146216 A2 | 12/2009 |
| WO | WO 2009/146218 A2 | 12/2009 |
| WO | WO 2009/151910 A2 | 12/2009 |
| WO | WO 2010/008744 A2 | 1/2010 |
| WO | WO 2010/011782 A1 | 1/2010 |
| WO | WO 2010/045318 A1 | 4/2010 |
| WO | WO 2010/048477 A2 | 4/2010 |
| WO | WO 2010/054051 A1 | 5/2010 |
| WO | WO 2010/085845 A1 | 8/2010 |
| WO | WO 2010/091140 A1 | 8/2010 |
| WO | WO 2010/098627 A2 | 9/2010 |

(56) References Cited

FOREIGN PATENT DOCUMENTS

| WO | WO 2010/104406 A1 | 9/2010 |
| --- | --- | --- |
| WO | WO 2010/117633 A1 | 10/2010 |
| WO | WO 2010/120861 A1 | 10/2010 |
| WO | WO 2010/124009 A2 | 10/2010 |
| WO | WO 2010/129053 A2 | 11/2010 |
| WO | WO 2011/002857 A2 | 1/2011 |
| WO | WO 2011/008053 A2 | 1/2011 |
| WO | WO 2011/008054 A2 | 1/2011 |
| WO | WO 2011/025267 A2 | 3/2011 |
| WO | WO 2011/025269 A2 | 3/2011 |
| WO | WO 2011/025271 A2 | 3/2011 |
| WO | WO 2011/038467 A1 | 4/2011 |
| WO | WO 2011/056741 A2 | 5/2011 |
| WO | WO 2011/060206 A2 | 5/2011 |
| WO | WO 2011/069962 A1 | 6/2011 |
| WO | WO 2011/070499 A1 | 6/2011 |

OTHER PUBLICATIONS

Boyd et al., "Lapatanib: Oncolytic dual EFGR and erbB-2 inhibitor," Drugs of the Future, 30:1225-1239 (2005).

Burstein et al., 2007 Poster presented at the SABCS, San Antonio, TX.

Chonn et al., "Recent advances in liposomal drug-delivery systems," Curr. Opin. Biotechnol., 6:698-708 (1995).

Eyles, "Oral delivery and fate of poly(lactic acid) microsphere-encapsulated interferon in rats," J. Pharm. Pharmacol., 49:669-674 (1997).

Gao et al., "Controlled release of a contraceptive steroid from biodegradable and injectable gel formulations: in vitro evaluation," Pham. Res., 12:857-863 (1995).

Geyer et al., "Lapatinib plus capecitabine for HER2-positive advanced breast cancer," N. Engl. J. Med., 355:2733-2743 (2006).

Heymach et al., "Epidermal growth factor receptor inhibitors in development for the treatment of non-small cell lung cancer," Clin. Cancer Res., 12:4441s-4445s (2006).

Jackisch, "Challenges in the treatment of ErbB2 (HER2)-positive breast cancer," EJC Supplements, 6:7-14 (2008).

Jallal et al., "A Src/Abl kinase inhibitor, SKI-606, blocks breast cancer invasion, growth, and metastasis in vitro and in vivo," Cancer Res., 67:1580-1588 (2007).

Lorusso et al., "Therapeutic potential of novel selective-spectrum kinase inhibitors in oncology," Expert Opin. Investig. Drugs, 17:1013-1028 (2008).

Lou et al., "Progress in target therapy for breast cancer," J. Oncology, (2009),15:788-795 (English abstract).

Meyerhardt et al., "Phase II study of capecitabine, oxaliplatin, and erlotinib in previously treated patients with metastastic colorectal cancer," J. Clin. Oncol., 24:1892-1897 (2006).

Nole et al., "Dose-finding and pharmacokinetic study of an all-oral combination regimen of oral vinorelbine and capecitabine for patients with metastatic breast cancer," Ann. Oncol., 17:322-329 (2006).

Ocana et al., "Identifying breast cancer druggable oncogenic alternations: Lessons learned and future targeted options," Clin. Cancer Res., 14:961-970 (2008).

Ostro et al., "Use of liposomes as injectable-drug delivery system," Am. J. Hosp. Pharm., 46:1576-1587 (1989).

Ouchi et al., "Antitumor activity of erlotinib in combination with capecitabine in human tumor xenograft models," Cancer Chemother. Pharmacol., 57:693-702 (2006).

Parkin et al., "Use of statics to assess the global burden of breast cancer," Breast J., 12(Suppl 1):S70-80 (2006).

Pegram, et al., "The molecular and cellular biology of HER2/neu gene amplification/overexpression and the clinical development of herceptin (Trastuzumab) therapy for breast cancer," Cancer Treatment and Research,103:57-75 (2000).

Rabindran et al., "Antitumor activity of HKI-272, an orally active, irreversible inhibitor of the HER-2 tyrosine kinase," Cancer Res., 64:3958-3965 (2004).

Rampaul et al., "Clinicial value of epidermal growth factor receptor expression in primary breast cancer," Adv. Anat. Pathol., 12:271-273 (2005).

Rao, "Recent developments of collagen-based materials for medical applications and drug delivery systems," J. Biomater Sci. Polym. Ed., 7:623-645 (1995).

Remington's Pharmaceutical Science, 17th Edition, ed. Alfonso R. Gennaro, Mack Publishing Company, Easton, PA (1985).

Reid et al., "Dual inhibition of ErbB1 (EGFR/HER1) and ErbB2 (HER2/neu)," Eur. J. Cancer, 43:481-489 (2007).

Saura et al., "Safety and efficacy of neratinib in combination with capecitabine in patients with ErbB2-positive breast cancer," Thirty-Fourth Annual CTRC-AACR San Antonio Breast Cancer Symposium, Dec. 6-10, Abstract # P1-12-09, (2011).

Smith, "Goals of treatment of patients with metastatic breast cancer," Seminars in Oncology, 33(1 Suppl 2):S2-5 (2006).

Twelves et al., "Erlotinib in combination with capecitabine and docetaxel in patients with metastatic breast cancer: a dose-escalation study," Eur. J. Cancer, 44:419-426 (2008).

Walko et al., "Capecitabine: a review," Clin. Ther., 27:23-44 (2005).

Xia, "Truncated ErbB2 receptor (p95ErbB2) is regulated by heregulin through heterodimer formation with ErB3 yet remains sensitive to the dual EGFR/ErB2 kinase inhibitor GW572016," Oncogene, 23:646-653 (2004).

Zaczek et al., "The diverse signaling network of EGFR, HER2, HER3 and HER4 tyrosine kinase receptors and the consequences for therapeutic approaches," Histol. Histopathol., 20:1005-1015 (2005).

Glaxosmithkline, Tykerb prescription label, 2010; Retrieved on Apr. 30, 2014, from the Internet <URL: http://www.accessdata.fda.gov/drugsatfda__docs/label/2010/022059s0071b1.pdf>, pp. 1-25.

"Trastuzumab." Wikipedia: Wikipedia: The Free Encyclopedia. Wikimedia Foundation, Inc. Retrieved from the Internet Aug. 14, 2009. URL:http://en.wikipedia.org/wiki/Herceptin.

Abbas et al., "A Drug Interaction Study to Evaluate the Effect of Ketoconazole on the Pharmacokinetics (PK) of Neratinib in Healthy Subjects," Clin. Pharmacol. Therapeutics 85:s44 (2009).

Abbas et al., "Evaluation of Neratinib (HKI-272) and Paclitaxel Pharmacokinetics (PK) in Asian and Caucasian Patients with Erbb2+ Breast Cancer: a Phase ½ Study of Neratinib in Combination with Paclitaxel," Ann. Oncol. 21:101 (2010).

Abbas et al., "Pharmacokinetics of Oral Neratinib During Co-Administration of Ketoconazole in Healthy Subjects," Br. J. Clin. Pharmacol. 71(4):522-527 (2011).

Abbas-Borhan et al., "A Clinical Study to Characterize the Occurrence of Mild-To-Moderate Diarrhea After Administration of Neratinib Either Once Daily or Twice Daily for 14 Days," EJC Suppl. 8:143 (2010).

Abbas-Borhan et al., "An Open-Label Study to Assess the Mass Balance and Metabolic Disposition of an Orally Administered Single Dose of 14C-Labeled Neratinib, an Irreversible pan-ErbB inhibitor, in Healthy Subjects," Drug Metab. Rev. 42:S1, 216 Abstr. P330 (2010).

Abrams et al., "Preclinical evaluation of the tyrosine kinase inhibitor SU11248 as a single agent and in combination with "standard of care" therapeutic agents for the treatment of breast cancer," Mol. Cancer Ther. 2(10):1011-1021 (2003).

Abramson and Arteaga, "New Strategies in HER2-Overexpressing Breast Cancer: Many Combinations of Targeted Drugs Available," Clin. Cancer Res. 17:952-958 (2011).

Adelaide et al., "Integrated Profiling of Basal and Luminal Breast Cancers," Cancer Res. 67(24):11565-11575 (2007).

Al-Dasooqi et al., "HER2 Targeted Therapies for Cancer and the Gastrointestinal Tract," Curr. Drug Targets 10(6):537-542 (2009).

Ali et al., "Mutational Spectra of PTEN/MMAC1 Gene: a Tumor Suppressor with Lipid Phosphatase Activity," J. Natl. Cancer Inst. 91(22):1922-1932 (1999).

Allegra et al., "American Society of Clinical Oncology Provisional Clinical Opinion: Testing for KRAS Gene Mutations in Patients With Metastatic Colorectal Carcinoma to Predict Response to Anti-Epidermal Growth Factor Receptor Monoclonal Antibody Therapy," J. Clin. Oncol. 27(12):2091-2096 (2009).

Alvarez et al., "Emerging Targeted Therapies for Breast Cancer," J. Clin. Oncol. 28(20):3366-3379 (2010).

(56) References Cited

OTHER PUBLICATIONS

Álvarez, "Present and Future Evolution of Advanced Breast Cancer Therapy," Breast Cancer Res. 12(Suppl 2):S1 (2010).
Amslinger, "The tunable functionality of alpha,beta-unsaturated carbonyl compounds enables their differential application in biological systems," ChemMedChem. 5(3):351-356 (2010).
Andre and Diniz, "Targeted regimes without cytotoxics—are they ready for prime time?" EJC Suppl. 7:49 Abst. 191 (2009).
Anonymous: "Meeting Archives of Chemotherapy Foundation Symposium XXIV, Nov. 7-10, 2007", The Chemotherapy Foundation, Nov. 8, 2007, Retrieved from the Internet on Jan. 13, 2010: URL:http://www.chemotherapyfoundationsymposium.org/meeting_archives/meetingarchives_tcf2007_main.html.
Anonymous: "Anticancer Agent—neratinib", Manufacturing Chemist, Dec. 2010/Jan. 2011, p. 27.
Arteaga, "ErbB-targeted therapeutic approaches in human cancer," Exp. Cell. Res. 284(1):122-130 (2003).
Awada and Piccart-Gebhart, "Management of HER-2/Neu-Positive Metastatic Breast Cancer," Eur. J. Cancer (Suppl. 6):2-9 (2008).
Awada et al., "Safety and Efficacy of Neratinib (HKI-272) in Combination with Vinorelbine in ErbB2+ Metastatic Breast Cancer," Cancer Res. 69:24(Suppl 3) Abstr. 5095 (2009).
Awada et al., "Safety and Efficacy of Neratinib (HKI-272) in Combination with Vinorelbine in ErbB2+ Metastatic Breast Cancer (MBC)," Ann. Oncol. 21(Suppl. 4):iv62-iv63 Abstr. 145P (2010).
Azria et al., "[Radiotherapy and inhibitors of epidermal growth factor receptor: preclinical findings and preliminary clinical trials]," Bull Cancer 90 Spec No. S202-S212 (2003). (Abstract only).
Badache and Goncalves, "The ErbB2 signaling network as a target for breast cancer therapy," J. Mammary Gland Biol. Neoplasia 11(1):13-25 (2006).
Barton et al., "Predictive molecular markers of response to epidermal growth factor receptor(EGFR) family-targeted therapies," Curr. Cancer Drug Targets 10(8):799-812 (2010).
Baselga and Swain, "Novel anticancer targets: revisiting ERBB2 and discovering ERBB3," Nat. Rev. Cancer 9(7):463-475 (2009) (Epub Jun. 18, 2009).
Baselga, "Is there a role for the irreversible epidermal growth factor receptor inhibitor EKB-569 in the treatment of cancer? A mutation-driven question," J. Clin. Oncol. 24(15):2225-2226 (2006).
Baselga, "Novel agents in the era of targeted therapy: what have we learned and how has our practice changed?" Ann. Oncol. 19(Suppl 7):vii281-vii288 (2008).
Baselga, "Treatment of HER2-Overexpressing Breast Cancer," Ann. Oncol. (Suppl 7):vii36-vii40 (2010).
Bayes et al., "Gateways to clinical trials," Methods Find. Exp. Clin. Pharmacol. 28(9):657-678 (2006).
Bedard et al., "Beyond trastuzumab: overcoming resistance to targeted HER-2 therapy in breast cancer," Curr. Cancer Drug Targets 9(2):148-162 (2009).
Bedard et al., "Stemming resistance to HER-2 targeted therapy," J. Mammary Gland Biol. Neoplasia 14(1):55-66 (2009) (Epub Mar. 4, 2009).
Belani, "The role of irreversible EGFR inhibitors in the treatment of non-small cell lung cancer: overcoming resistance to reversible EGFR inhibitors," Cancer Invest. 28(4):413-423 (2010).
Bell and Haber, "A blood-based test for epidermal growth factor receptor mutations in lung cancer," Clin. Cancer Res. 12(13):3875-3877 (2006).
Berns et al., "A functional genetic approach identifies the PI3K pathway as a major determinant of trastuzumab resistance in breast cancer," Cancer Cell 12(4):395-402 (2007).
Berz and Wanebo, "Targeting the growth factors and angiogenesis pathways: small molecules in solid tumors," J. Surg. Oncol. 103(6):574-586 (2011).
Besse et al., "Neratinib (HKI-272), an irreversible pan-ErbB receptor tyrosine kinase inhibitor: preliminary results of a phase 2 trial in patients with advanced non-small cell lung cancer," Eur. J. Cancer (Suppl.):23 Abstr. 203 (2008).
Besse et al., "Targeted therapies in lung cancer," Ann. Oncol. 18(Suppl. 9):ix135-ix142 (2007).
Bettendorf et al., "Chromosomal imbalances, loss of heterozygosity, and immunohistochemical expression of TP53, RB1, and PTEN in intraductal cancer, intraepithelial neoplasia, and invasive adenocarcinoma of the prostate," Genes Chromosomes Cancer 47(7):565-572 (2008).
Bischoff and Ignatov, "The Role of Targeted Agents in the Treatment of Metastatic Breast Cancer," Breast Care (Basel) 5(3):134-141 (2010) (Epub Jun. 16, 2010).
Blanco-Aparicio et al., "PTEN, More Than the AKT Pathway," Carcinogenesis 28(7):1379-1386 (2007) (Epub Mar. 6, 2007).
Blencke et al., "Mutation of threonine 766 in the epidermal growth factor receptor reveals a hotspot for resistance formation against selective tyrosine kinase inhibitors," J. Biol. Chem. 278(17):15435-15440 (2003) (Epub Feb. 19, 2003).
Board et al., "Multiplexed assays for detection of mutations in PIK3CA," Clin. Chem 54(4):757-760 (2008).
Bonanno et al., "Mechanisms of acquired resistance to epidermal growth factor receptor tyrosine kinase inhibitors and new therapeutic perspectives in non small cell lung cancer," Curr. Drug Targets 12(6):922-933 (2011).
Boschelli, "4-Anilino-3-quinolinecarbonitriles: An Emerging Class of Kinase Inhibitors—An Update," Med. Chem Rev. Online 1:457-463 (2004).
Bose and Ozer, "Neratinib: an oral, irreversible dual EGFR/HER2 inhibitor for breast and non-small cell lung cancer," Expert Opin. Investig. Drugs 18(11):1735-1751 (2009).
Bose et al., "Allelic loss of chromosome 10q23 is associated with tumor progression in breast carcinomas," Oncogene 17(1):123-127 (1998).
Bose et al., "Reduced expression of PTEN correlates with breast cancer progression," Hum. Pathol. 33(4):405-409 (2002).
Boyce et al., "Requirement of pp60c-src expression for osteoclasts to form ruffled borders and resorb bone in mice," J. Clin. Invest. 90(4):1622-1627 (1992).
Brackstone et al., "Canadian initiatives for locally advanced breast cancer research and treatment: inaugural meeting of the Canadian Consortium for LABC," Curr. Oncol. 18(3):139-144 (2011).
Bridges, "Current Progress Towards the Development of Tyrosine Kinase Inhibitors as Anticancer Agents," Expert Opin. Emerg. Drugs. 3:279-292 (1998).
Brittain, Harry G. (Eds), "Polymorphism in Pharmaceutical Solids", Chapters 1 and 5, Marcel Dekker, Inc., New York (1999).
Brook et al., "Management of transitional cell carcinoma by targeting the epidermal growth factor receptor," Therapy 3(3):407-416 (2006).
Browne et al., "HER-2 Signaling and Inhibition in Breast Cancer," Curr. Cancer Drug Targets 9(3):419-438 (2009).
Broxterman and Georgopapadakou, "Anticancer therapeutics: a surge of new developments increasingly target tumor and stroma," Drug Resist. Updat. 10(4-5):182-193 (2007) (Epub Sep. 12, 2007).
Buerger et al., "Allelic length of a CA dinucleotide repeat in the egfr gene correlates with the frequency of amplifications of this sequence—first results of an inter-ethnic breast cancer study," J. Pathol. 203(1):545-550 (2004).
Bullard Dunn et al., "Evolving Therapies and FAK Inhibitors for the Treatment of Cancer," Anticancer Agents Med. Chem. 10(10):722-734 (2010).
Burstein et al., "Gastrointestinal and Cardiovascular Safety Profiles of Neratinib Monotherapy in Patients with Advanced Erbb2-Positive Breast Cancer," Cancer Res. 69:Abst 5096 (2009).
Burstein et al., "HKI-272, an irreversible pan erbB receptor tyrosine kinase inhibitor: preliminary phase 2 results in patients with advanced breast cancer," Breast Cancer Res. Treat. 106:S268 Abstr. 6061 (2007).
Burstein et al., "Neratinib (HKI-272), an irreversible pan ErbB receptor tyrosine kinase inhibitor: phase 2 results in patients with advanced HER2+ breast cancer," Cancer Res. 69(2 Suppl.) Abstr. 37 (2009).
Burstein et al., "Neratinib, an irreversible ErbB receptor tyrosine kinase inhibitor, in patients with advanced ErbB2-positive breast cancer," J. Clin. Oncol. 28(8):1301-1307 (2010).
Burstein, "The Distinctive Nature of HER2-Positive Breast Cancers," N. Engl. J. Med. 353(16):1652-1654 (2005).

(56) References Cited

OTHER PUBLICATIONS

Byrn et al., "Pharmaceutical solids: a strategic approach to regulatory considerations," Pharm. Res. 12(7):945-954 (1995).
Callahan and Hurwitz, "Human epidermal growth factor receptor-2-positive breast cancer: Current management of early, advanced, and recurrent disease," Curr. Opin. Obstet. Gynecol. 23(1):37-43 (2011).
Camp et al., "Molecular mechanisms of resistance to therapies targeting the epidermal growth factor receptor," Clin. Cancer Res. 11(1):397-405 (2005).
Campas et al., "BIBW-2992. Dual EGFR/HER2 Inhibitor Oncolytic;Tovok™," Drugs Future 33(8):649-654 (2008).
Campbel et al., "Gefitinib for the Treatment of Non-Small-Cell Lung Cancer," Expert Opin. Pharmacother. 11(8):1343-1357 (2010).
Cao et al., "Epidermal Growth Factor Receptor as a Target for Anti-Cancer Agent Design," Anticancer Agents Med. Chem. 10(6):491-503 (2010).
Cappuzzo et al., "Surrogate predictive biomarkers for response to anti-EGFR agents: state of the art and challenges," Int. J. Biol. Markers 22(1 Suppl 4):S10-S23 (2007).
Cardoso et al., "Locally Recurrent or Metastatic Breast Cancer: ESMO Clinical Practice Guidelines for Diagnosis, Treatment and Follow-Up," Ann. Oncol. 21(5):v15-v19 (2010).
Carney et al., "HER-2/neu diagnostics in breast cancer," Breast Cancer Res. 9(3):207 (2007).
Carter et al., "Small-Molecule Inhibitors of the Human Epidermal Receptor Family," Expert Opin. Investig. Drugs 18(12):1829-1842 (2009).
Cascone et al., "Epidermal Growth Factor Receptor Inhibitors in Non-Small-Cell Lung Cancer," Expert Opin. Drug Discov. 2(3):335-348 (2007).
Chan and Giaccia, "Harnessing Synthetic Lethal Interactions in Anticancer Drug Discovery," Nat. Rev. Drug Discov. 10(5):351-364 (2011).
Chandrasekaran et al., "Reversible Covalent Binding of Neratinib to Human Serum Albumin in Vitro," Drug Metab. Lett. 4(4):220-227 (2010).
Chen et al., "Epidermal growth factor receptor inhibitors: current status and future directions," Curr. Probl. Cancer 33(4):245-294 (2009).
Chenoweth, "Can single-patient investigational new drug studies hurry slow trains to the fast track?" Drug Discov. Today 11(5-6):185-186 (2006).
Cheung and Paterson, "American Chemical Society—226th National Meeting. Pain and Oncology," Idrugs 6(10):935-936 (2003).
Chien and Rugo, "The Cardiac Safety of Trastuzumab in the Treatment of Breast Cancer," Expert Opin. Drug Saf. 9(2):335-346 (2010).
Cho et al., "Structure of the extracellular region of HER2 alone and in complex with the Herceptin Fab," Nature 421(6924):756-760 (2003).
Chow et al., "Safety and efficacy of neratinib (HKI-272) in combination with paclitaxel in ErbB2+ metastatic breast cancer," Cancer Res. (Meeting Abstracts) 69:S5081 (2009).
Chow et al., "Safety and efficacy of neratinib (HKI-272) in combination with paclitaxel in patients with solid tumors," J. Clin. Oncol. (Meeting Abstracts) 27(15S):3557 (2009).
Chow et al., "Safety and efficacy of neratinib (HKI-272) in combination with paclitaxel in ERBB2+ metastatic breast cancer (MBC)," Ann. Oncol. 21(Suppl 4):iv62 Abstr. 144P (2010).
Cicenas, "The Potential Role of the EGFR/ERBB2 Heterodimer in Breast Cancer," Expert Opin. Ther. Patents 17(6):607-616 (2007).
Clouser et al., "Biomarker Targets and Novel Therapeutics," Cancer Treat. Res. 149:85-105 (2009).
Cobleigh et al., "Multinational study of the efficacy and safety of humanized anti-HER2 monoclonal antibody in women who have HER2-overexpressing metastatic breast cancer that has progressed after chemotherapy for metastatic disease," J. Clin. Oncol. 17(9):2639-2648 (1999).
Collins et al., "Lapatinib: a competitor or companion to trastuzumab?" Cancer Treat. Rev. 35(7):574-581 (2009).
Colombo et al., "HER2 targeting as a two-sided strategy for breast cancer diagnosis and treatment: Outlook and recent implications in nanomedical approaches," Pharmacol. Res. 62(2):150-165 (2010) (Epub Feb. 1, 2010).
Cooper and Cohen, "Mechanisms of resistance to EGFR inhibitors in head and neck cancer," Head Neck 31(8):1086-1094 (2009).
Cortes-Funes et al., "Neratinib, An Irreversible Pan Erb Receptor Tyrosine Kinase Inhibitor Active for Advanced HER2+ Breast Cancer," Breast Cancer Res. 11 Suppl 1:S19 (2009).
Coughlin et al., "Approaches and limitations of phosphatidylinositol-3-kinase pathway activation status as a predictive biomarker in the clinical development of targeted therapy," Breast Cancer Res. Treat. 124(1):1-11 (2010) (Epub Aug. 28, 2010).
Cox, "Regression Models and Life Tables (With Discussion)," Journal of the Royal Statistical Society. Series B (Methodological), vol. 34, No. 2. (1972), pp. 187-220.
Da Cunha Santos et al., "EGFR Mutations and Lung Cancer," Ann. Rev. Pathol. 6:49-69 (2011).
Damia and D'Incalci, "Contemporary pre-clinical development of anticancer agents—what are the optimal preclinical models?" Eur. J. Cancer 45(16):2768-2781 (2009) (Epub Sep. 15, 2009).
Dancey, "Epidermal growth factor receptor inhibitors in non-small cell lung cancer," Drugs 67(8):1125-1138 (2007).
Dang et al.,"The safety of dose-dense doxorubicin and cyclophosphamide followed by paclitaxel with trastuzumab in HER-2/neu overexpressed/amplified breast cancer," J. Clin. Oncol. 26(8):1216-1222 (2008).
Daniele and Sapino, "Anti-HER2 treatment and breast cancer: state of the art, recent patents, and new strategies," Recent Pat. Anticancer Drug Discov. 4(1):9-18 (2009).
Davidson, "HER2-Targeted Therapies: How Far We've Come-And Where We're Headed," Oncology (Williston Park) 25(5):425-426 (2011).
Davoli et al., "Progression and Treatment of HER2-Positive Breast Cancer," Cancer Chemother. Pharmacol. 65(4):611-623 (2010) (Epub Dec. 20, 2009).
De Bono and Rowinsky, "The ErbB receptor family: a therapeutic target for cancer," Trends Mol. Med. 8(4 Suppl):S19-S26 (2002).
De Luca and Normanno, "Predictive biomarkers to tyrosine kinase inhibitors for the epidermal growth factor receptor in non-small-cell lung cancer," Curr. Drug Targets 11(7):851-864 (2010).
De Seranno and Meuwissen, "Progress and Applications of Mouse Models for Human Lung Cancer," Eur. Respir. J. 5(2):426-443 (2010).
Depowski et al., "Loss of expression of the PTEN gene protein product is associated with poor outcome in breast cancer," Mod. Pathol. 14(7):672-676 (2001).
Di Cosimo and Baselga, "Management of breast cancer with targeted agents: importance of heterogeneity. [corrected]." Nat. Rev. Clin. Oncol. 7(3):139-147 (2010) (Epub Feb. 2, 2010).
Di Cosimo and Baselga, "Targeted Therapies in Breast Cancer: Where Are We Now?" Eur. J. Cancer 44(18):2781-2790 (2008) (Epub Nov. 14, 2008).
Di Maio et al., "New drugs in advanced non-small-cell lung cancer: searching for the correct clinical development," Expert Opin. Investig. Drugs 19(12):1503-1514 (2010) (Epub Nov. 4, 2010).
Dickler, "Updates on Therapeutic Approaches in HER2-Positive Disease," Clin. Adv. Hematol. Oncol. 8(2):105-107 (2010).
Dinh et al., "Trastuzumab for early breast cancer: current status and future directions," Clin. Adv. Hematol. Oncol. 5(9):707-717 (2007).
Dirix et al., "Neratinib Monotherapy in Patients with Advanced ERBB2-Positive Breast Cancer: Gastrointestinal and Cardiovascular Safety Profiles," Ann. Oncol. 21(Suppl 4):iv61-iv62 Abstr. 141P (2010).
Doebele et al., "New strategies to overcome limitations of reversible EGFR tyrosine kinase inhibitor therapy in non-small cell lung cancer," Lung Cancer 69(1):1-12 (2010) (Epub Jan. 25, 2010).
Dorland's Illustrated Medical Dictionary. 31st ed. Philadelphia: Saunders Elsevier; c2007. Carcinoma; pp. 295-297.
Dowsett and Dunbier, "Emerging Biomarkers and New Understanding of Traditional Markers in Personalized Therapy for Breast Cancer," Clin. Cancer Res. 14(24):8019-8026 (2008).

(56) References Cited

OTHER PUBLICATIONS

Eck and Yun, "Structural and Mechanistic Underpinnings of the Differential Drug Sensitivity of EGFR Mutations in Non-Small Cell Lung Cancer," Biochim. Biophys. Acta 1804(3):559-566 (2010).
Egloff and Grandis, "Targeting epidermal growth factor receptor and SRC pathways in head and neck cancer," Semin. Oncol. 35(3):286-297 (2008).
Einhorn et al., "Summary Report 7th Annual Targeted Therapies of the Treatment of Lung Cancer," J. Thorac. Oncol. 3(5):545-555 (2008).
Einhorn, "Perspective on the Development of New Agents in Thoracic Cancers," Lung Cancer 50 Suppl 1:S27-S28 (2005).
Ellis and Crowder, "PIKing" the winner for phosphatidylinositol 3-kinase inhibitors in ErbB2-positive breast cancer: let's not "PTENed" it's easy! Clin. Cancer Res. 13(19):5661-5662 (2007).
Engelman and Settleman, "Acquired Resistance to Tyrosine Kinase Inhibitors During Cancer Therapy," Curr. Opin. Genet. Dev. 18(1):73-79 (2008) (Epub Mar. 5, 2008).
Engelman, "Targeting PI3K Signalling in Cancer: Opportunities, Challenges and Limitations," Nat. Rev. Cancer 9(8):550-562 (2009).
Engleman and Jänne, "Mechanisms of acquired resistance to epidermal growth factor receptor tyrosine kinase inhibitors in non-small cell lung cancer," Clin. Cancer Res. 14(10):2895-2899 (2008).
Ercan et al., "Amplification of EGFR T790M causes resistance to an irreversible EGFR inhibitor," Oncogene. 29(16):2346-2356 (2010) (Epub Feb. 1, 2010).
Esteva et al., "Molecular predictors of response to trastuzumab and lapatinib in breast cancer," Nat. Rev. Clin. Oncol. 7(2):98-107 (2010) (Epub Dec. 22, 2009).
Farley and Birrer, "Novel Therapeutic Targets," Cancer Treat. Res. 149:63-84 (2009).
Felip et al., "Emerging Drugs for Non-Small-Cell Lung Cancer," Expert Opin. Emerg. Drugs 12(3):449-460 (2007).
Ferron et al., "Oral bioavailability of pantoprazole suspended in sodium bicarbonate solution," Am. J. Health Syst. Pharm. 60(13):1324-1329 (2003).
Ferté et al., "Molecular circuits of solid tumors: prognostic and predictive tools for bedside use," Nat. Rev. Clin. Oncol. 7(7):367-380 (2010) (Epub Jun. 15, 2010).
Fleming et al., "Nitrile-containing pharmaceuticals: efficacious roles of the nitrile pharmacophore," J. Med. Chem. 53(22)7902-7917 (2010) (Epub Aug. 30, 2010).
Folkman, "Angiogenesis in cancer, vascular, rheumatoid and other disease," Nat. Med. 1(1):27-31 (1995).
Früh, "The search for improved systemic therapy of non-small cell lung cancer—what are today's options?" Lung Cancer 72(3):265-270 (2011) (Epub Apr. 14, 2011).
Fry, "Inhibition of the epidermal growth factor receptor family of tyrosine kinases as an approach to cancer chemotherapy: progression from reversible to irreversible inhibitors," Pharmacol. Ther. 82(2-3):207-218 (1999).
Gadji et al., "EGF receptor inhibitors in the treatment of glioblastoma multiform: old clinical allies and newly emerging therapeutic concepts," Eur. J. Pharmacol. 625(1-3):23-30 (2009) (Epub Oct. 18, 2009).
Gajria and Chandarlapaty, "HER2-amplified breast cancer: mechanisms of trastuzumab resistance and novel targeted therapies," Expert Rev. Anticancer Ther. 11(2):263-275 (2011).
Gajria et al., "Tolerability and Efficacy of Targeting Both mTOR and HER2 Signaling in Trastuzumab-Refractory HER2+ Metastatic Breast Cancer," San Antonio Breast cancer Symposium. Abstract P5-18-04 (2010).
Garcia et al., "Promoter Methylation of the PTEN Gene Is a Common Molecular Change in Breast Cancer," Genes Chromosomes Cancer 41(2):117-127 (2004).
Garrett and Arteaga, "Resistance to HER2-directed antibodies and tyrosine kinase inhibitors: mechanisms and clinical implications," Cancer Biol. Ther. 11(9):793-800 (2011) (Epub May 1, 2011).
Gatzemeier, "Second-Generation EGFR Inhibitors and Combinations," J. Thorac Oncol. 4(9): S121 (2009).

Gazdar, "Activating and Resistance Mutations of EGFR in Non-Small-Cell Lung Cancer: Role in Clinical Response to EGFR Tyrosine Kinase Inhibitors," Oncogene 28:S24-S31 (2009).
Genentech, Herceptin® -Product Literature, www.Genetech.com, Sep. 1998 Revised (Jun. 2014), pp, 1-35.
Geuna et al., "Hitting multiple targets in HER2-positive breast cancer: proof of principle or therapeutic opportunity?" Expert Opin. Pharmacother. 12(4):549-565 (2011) (Epub Jan. 6, 2011).
Ghayad and Cohen, "Inhibitors of the PI3K/Akt/mTOR pathway: new hope for breast cancer patients," Recent Pat. Anticancer Drug Discov. 5(1):29-57 (2010).
Giamas et al., "Kinases as Targets in the Treatment of Solid Tumors," Cell. Signal. 22(7):984-1002 (2010) (Epub Jan. 21, 2010).
Glück, "Chemotherapy Regimens in Metastatic Breast Cancer," Clin. Adv. Hematol. Oncol. 9(1):47-48 (2011).
Godin-Heymann et al., "Oncogenic activity of epidermal growth factor receptor kinase mutant alleles is enhanced by the T790M drug resistance mutation," Cancer Res. 67(15):7319-7326 (2007).
Godin-Heymann et al., "The T790M "gatekeeper" mutation in EGFR mediates resistance to low concentrations of an irreversible EGFR inhibitor," Mol. Cancer Ther. 7(4):874-879 (2008).
Goldhirsch et al., "2 years versus 1 year of adjuvant trastuzumab for HER2-positive breast cancer (HERA): an open-label, randomised control trail," Lancet 382:1021-1028 (2013).
Govindan, "A review of epidermal growth factor receptor/HER2 inhibitors in the treatment of patients with non-small-cell lung cancer," Clin. Lung Cancer 11(1):8-12 (2010).
Grimm et al., "Diagnostic and Therapeutic Use of Membrane Proteins in Cancer Cells," Curr. Med. Chem. 18(2):176-190 (2011).
Guarneri et al., "Anti-HER2 neoadjuvant and adjuvant therapies in HER2 positive breast cancer," Cancer Treat. Rev. 36 Suppl 3:S62-S66 (2010).
Gullick et al., "Expression of epidermal growth factor receptors on human cervical, ovarian, and vulval carcinomas," Cancer Res. 46(1):285-292 (1986).
Hager et al., "PTEN expression in renal cell carcinoma and oncocytoma and prognosis," Pathology 39(5):482-485 (2007) (Abstract Only).
Hammerman et al., "Resistance to Epidermal Growth Factor Receptor Tyrosine Kinase Inhibitors in Non-Small Cell Lung Cancer," Clin. Cancer Res. 15(24):7502-7509 (2009).
Harris et al., "c-erbB-2 in serum of patients with breast cancer," Int. J. Biol. Markers 14(1):8-15 (1999).
Hasselblatt, "Ependymal Tumors," Recent Results Cancer Res. 171:51-66 (2009).
Hawkins and Grunberg, "Chemotherapy-Induced Nausea and Vomiting: Challenges and Opportunities for Improved Patient Outcomes," Clin. J. Oncol. Nurs. 13(1):54-64 (2009).
Hegedus et al., "Interaction of ABC multidrug transporters with anticancer protein kinase inhibitors: substrates and/or inhibitors?" Curr. Cancer Drug Targets 9(3):252-272 (2009).
Heigener and Reck, "Mutations in the epidermal growth factor receptor gene in non-small cell lung cancer: Impact on treatment beyond gefitinib and erlotinib," Adv. Ther. 28(2):126-133 (2011) (Epub Dec. 16, 2010).
Heigener, "Non-Small Cell Lung Cancer in Never-Smokers: a New Disease Entity?" Onkologie 34(4):202-207 (2011) (Epub Mar. 18, 2011).
Higa et al., "Biological considerations and clinical applications of new HER2-targeted agents," Expert Rev. Anticancer Ther. 10(9):1497-1509 (2010).
Ho and Laskin, "EGFR-directed therapies to treat non-small-cell lung cancer," Expert Opin. Investig. Drugs 18(8):1133-1145 (2009).
Holbro and Hynes, "ErbB receptors: directing key signaling networks throughout life," Annu. Rev. Pharmacol. Toxicol. 44:195-217 (2004).
Holodov and Yakovlev, Clinical Pharmacokinetics, Moscow, Medicine, (1985), pp. 83-98, 134-138, 160, 378-380 (English translation not available).
Hookes and Lakeram, "American Chemical Society—235th National Meeting. Part 2: EGFR kinase inhibitors and β3-lactamases under investigation by Wyeth" Idrugs 11(6):391-393 (2008).

(56) References Cited

OTHER PUBLICATIONS

Horn and Sandler, "Epidermal growth factor receptor inhibitors and antiangiogenic agents for the treatment of non-small cell lung cancer," Clin. Cancer Res. 15(16):5040-5048 (2009) (Epub Aug. 11, 2009).

Hou and Kumamoto, "Flavonoids as protein kinase inhibitors for cancer chemoprevention: direct binding and molecular modeling," Antioxid. Redox Signal. 13(5):691-719 (2010).

Huang et al., "Up-regulation of miR-21 by HER2/neu signaling promotes cell invasion," J. Biol. Chem. 284(27):18515-18524 (2009) (Epub May 6, 2009).

Hubalek et al., "Resistance to HER2-targeted therapy: mechanisms of trastuzumab resistance and possible strategies to overcome unresponsiveness to treatment," Wien. Med. Wochenschr. 160(19-20):506-512 (2010) (Epub Oct. 26, 2010).

Huber et al., "Pharmacokinetics of pantoprazole in man," Int. J. Clin. Pharmacol. Ther. 34(5):185-194 (1996).

Hug et al., "A single-dose, crossover, placebo- and moxifloxacin-controlled study to assess the effects of neratinib (HKI-272) on cardiac repolarization in healthy adult subjects," Clin. Cancer Res. 16(15):4016-4023 (2010) (Epub Jul. 20, 2010).

Hung and Lau, "Basic Science of HER-2/neu: a review," Semin. Oncol. 26(4 Suppl 12):51-59 (1999).

Hynes and Lane, "ERBB Receptors and Cancer: the Complexity of Targeted Inhibitors," Nat. Rev. Cancer 5(5):341-354 (2005).

ICH Expert Working Group: Impurities in New Drug Substances Q3A(R2), "International Conference on Harmonisation of Technical Requirements for Registration of Pharmaceuticals for Human Use" (Online) 2006.

Ikediobi, "Somatic Pharmacogenomics in Cancer," Pharmacogenomics J. 8(5):305-314 (2008) (Epub Aug. 5, 2008).

Iliadis et al., "APIS: a software for model identification, simulation and dosage regimen calculations in clinical and experimental pharmacokinetics," Computer Methods Programs Biomed. 38(4):227-239 (1992).

International Preliminary Report on Patentability Chapter 1 for International Application No. PCT/US2009/047643 dated Dec. 18, 2010.

International Search Report for International Application No. PCT/US2008/080130, mailed Apr. 5, 2009.

International Search Report for International Patent Application No. PCT/US2009/047643, mailed Jan. 28, 2010.

Isakoff and Baselga, "Trastuzumab-DM1: building a chemotherapy-free road in the treatment of human epidermal growth factor receptor 2-positive breast cancer," J. Clin. Oncol. 29(4):351-354 (2011) (Epub Dec. 20, 2010).

Ito et al., "A Phase 1 Study of Neratinib (HKI-272) in Combination with Paclitaxel in Japanese Patients with Solid Tumors," Ann. Oncol. 21 (Suppl 8):viii103 Abstr. 298P (2010).

Ito et al., "Tolerability and safety of oral neratinib (HKI-272) in Japanese patients with advanced solid tumors," J. Clin. Oncol. 27:(suppl; abstr. e14505) (2009).

Jänne et al., "Phase I dose-escalation study of the pan-HER inhibitor, PF299804, in patients with advanced malignant solid tumors," Clin. Cancer Res. 17(5):1131-1139 (2011) (Epub Jan. 10, 2011).

Jänne, "Challenges of detecting EGFR T790M in gefitinib/erlotinib-resistant tumours," Lung Cancer 60 Suppl 2:S3-S9 (2008).

Jelliffe et al., "Adaptive control of drug dosage regimens: basic foundations, relevant issues, and clinical examples," Int. J. Biomed. Comput. 36(1-2):1-23 (1994).

Ji et al., "Epidermal growth factor receptor variant III mutations in lung tumorigenesis and sensitivity to tyrosine kinase inhibitors," Proc. Natl. Acad. Sci. U.S.A. 103(20):7817-7822 (2006) (Epub May 3, 2006).

Ji et al., "The impact of human EGFR kinase domain mutations on lung tumorigenesis and in vivo sensitivity to EGFR-targeted therapies," Cancer Cell. 9(6):485-495 (2006) (Epub May 25, 2006).

Jimeno and Hidalgo, "Pharmacogenomics of epiderman growth factor receptor (EGFR) tyrosine kinase inhibitors," Biochim. Biophys. Acta 1766(2):217-229 (2006) (Epub Sep. 12, 2006).

Johnson et al., "Impact of EGFR mutations on treatment of non-small cell lung cancer," Cancer Chemother. Pharmacol. 58(Suppl1): s5-s9 (2006).

Johnson et al., "Strategies for discovering and derisking covalent, irreversible enzyme inhibitors," Future Med. Chem. 2(6):949-964 (2010).

Johnson, "Biomarkers of Lung Cancer Response to EGFR-TKI," EJC Suppl. 5(8):14-15 Abstr. S23 (2007).

Johnson, "Protein kinase inhibitors: contributions from structure to clinical compounds," Q. Rev. Biophys. 42(1):1-40 (2009) (Epub Mar. 19, 2009).

Jones and Buzdar, "Evolving Novel Anti-HER2 Strategies," Lancet Oncol. 10(12):1179-1187 (2009).

Jones, "Adaptive trials receive boost," Nat. Rev. Drug Discov. 9(5):345-348 (2010) (Epub Apr. 23, 2010).

Jones, "HER4 intracellular domain (4ICD) activity in the developing mammary gland and breast cancer," J. Mammary Gland Biol. Neoplasia 13(2):247-258 (2008) (Epub May 13, 2008).

Jorissen et al., "Epidermal growth factor receptor: mechanisms of activation and signalling," Exp. Cell. Res. 284(1):31-53 (2003).

Joshi and Kucherlapati, "Pharmacogenomics of lung cancer: with a view to address EGFR-targeted therapies," Pharmacogenomics 8(9):1211-1220 (2007).

Kamath and Buolamwini, "Targeting EGFR and HER-2 receptor tyrosine kinases for cancer drug discovery and development," Med. Res. Rev. 26(5):569-594 (2006).

Kane, "Cancer Therapies Targeted to the Epidermal Growth Factor Receptor and Its Family Members," Expert Opin. Ther. Pat. 16(2):147-164 (2006).

Kaplan and Meier, "Nonparametric Estimation From Incomplete Observations," J. Am. Stat. Assoc. 53:457-481 (1958).

Katzel et al., "Recent advances of novel targeted therapy in non-small cell lung cancer," J Hematol. Oncool. 2:2 (2009).

Kennedy et al., "Novel Agents in the Management of Lung Cancer," Curr. Med. Chem. 17(35):4291-4325 (2010).

Kim et al., "Chasing targets for EGFR tyrosine kinase inhibitors in non-small-cell lung cancer: Asian perspectives," Expert Rev. Mol. Diagn.7(6):821-836 (2007).

Kim et al., "The role of HER-2 oncoprotein in drug-sensitivity in breast cancer (Review)," Oncol. Rep. 9(1):3-9 (2002).

Klein and Levitzki, "Targeting the EGFR and the PKB Pathway in Cancer," Curr. Opin. Cell. Biol. 21(2):185-193 (2009) (Epub Feb. 11, 2009).

Klüter et al., "Characterization of irreversible kinase inhibitors by directly detecting covalent bond formation: a tool for dissecting kinase drug resistance," ChemBioChem 11(18):2557-2566 (2010).

Kotteas et al., "Targeted therapy for nonsmall cell lung cancer: focusing on angiogenesis, the epidermal growth factor receptor and multikinase inhibitors," Anticancer Drugs 21(2):151-168 (2010).

Krop, "Managing Trastuzumab-resistant Breast Cancer," Clin. Adv. Hematol. Oncol. 7(2):108-110 (2009).

Kuznar, "New Small Molecule Added to Trastuzumab Improves Survival in Metastatic Disease," Am. Health Drug Benefits 2(5):27 (2009).

Kwak et al., "Irreversible inhibitors of the EGF receptor may circumvent acquired resistance to gefitinib," Proc. Natl. Acad. Sci. U.S.A. 102(21):7665-7670 (2005) (Epub May 16, 2005).

La Motta et al., "Computational studies of epidermal growth factor receptor: docking reliability, three-dimensional quantitative structure-activity relationship analysis, and virtual screening studies," J. Med. Chem. 52(4):964-975 (2009).

Laack et al., "Lessons learnt from gefitinib and erlotinib: Key insights into small-molecule EGFR-targeted kinase inhibitors in non-small cell lung cancer," Lung Cancer 69(3):259-264 (2010) (Epub Jun. 19, 2010).

Lam and Mok, "Targeted Therapy: An Evolving World of Lung Cancer," Respirology 16(1):13-21 (2011) (Epub Aug. 16, 2010).

Langer and Soria, "The role of anti-epidermal growth factor receptor and anti-vascular endothelial growth factor therapies in the treatment of non-small-cell lung cancer," Clin. Lung Cancer 11(2):82-90 (2010).

(56) References Cited

OTHER PUBLICATIONS

Leone and Dudek, "Enzyme replacement therapy for Gaucher's disease in patient treated for non-small cell lung cancer," Anticancer Res. 28(6B):3937-3939 (2008).
Levitzki and Mishani, "Tyrphostins and other tyrosine kinase inhibitors," Annu. Rev. Biochem. 75:93-109 (2006).
Li and Perez-Soler, "Skin toxicities associated with epidermal growth factor receptor inhibitors," Target. Oncol. 4(2):107-119 (2009) (Epub May 19, 2009).
Li et al., "BIBW2992, an irreversible EGFR/HER2 inhibitor highly effective in preclinical lung cancer models," Oncogene 27(34):4702-4711 (2008) (Epub Apr. 14, 2008).
Li et al., "PTEN, a putative protein tyrosine phosphatase gene mutated in human brain, breast, and prostate cancer," Science 275(5308):1943-1947 (1997).
Ligibel and Winer, "Trastuzumab/chemotherapy combinations in metastatic breast cancer," Semin. Oncol. 29(3 Suppl 11):38-43 (2002).
Limentani et al., "Safety and Efficacy of Neratinib (HKI-272) in Combination with Vinorelbine in Patients with Solid Tumors," J. Clin. Oncol. (Meeting Abstracts) 27(15S):e14554 (2009).
Lin and Winer, "Chemotherapy agents in human epidermal growth factor receptor 2-positive breast cancer: time to step out of the limelight," J. Clin. Oncol. 29(3):251-253 (2011) (Epub Dec. 13, 2010).
Lin and Yang, "Epidermal growth factor receptor tyrosine kinase inhibitors in elderly or poor performance status patients with advanced non-small cell lung cancer," Target. Oncol. 4(1):37-44 (2009) (Epub Jan. 20, 2009).
Linardou et al., "Somatic EGFR mutations and efficacy of tyrosine kinase inhibitors in NSCLC," Nat. Rev. Clin. Oncol. 6(6):352-366 (2009).
Little, "Molecular Tests, Targets and Therapies for Cancer," EPC (DIA 43rd Annual Meeting Edition) p. 98 (2007).
Liu et al., "Targeting epidermal growth factor receptor in lung cancer: Perspective from the Asia-Pacific region," Asia-Pac. J. Clin. Oncol. 2:22-31 (2006).
Locker et al., "ASCO 2006 update of recommendations for the use of tumor markers in gastrointestinal cancer," J. Clin. Oncol. 24(33):5313-5327 (2006) (Epub Oct. 23, 2006).
Loew et al., "The epidermal growth factor receptor as a therapeutic target in glioblastoma multiforme and other malignant neoplasms," Anticancer Agents Med. Chem. 9(6):703-715 (2009).
Loke, "Drug-drug interactions—bridging the gulf between the bench and the bedside?" Br. J. Clin. Pharmacol. 71(4):485-486 (2011).
LoPiccolo et al., "Targeting the PI3K/Akt/mTOR pathway: effective combinations and clinical considerations," Drug Resist. Updat. 11(1-2):32-50 (2008) (Epub Dec. 31, 2007).
Loriot et al., "Drug insight: gastrointestinal and hepatic adverse effects of molecular-targeted agents in cancer therapy," Nat. Clin. Pract. Oncol. 5(5):268-278 (2008) (Epub Mar. 18, 2008).
Loriot et al., "Pemetrexed-induced pneumonitis: a case report," Clin. Lung Cancer 10(5):364-366 (2009).
Lu and Ku, "Preformulation stability study of the EGFR inhibitor HKI-272 (Neratinib) and mechanism of degradation," Drug Dev. Ind. Pharm. 1-7 (2011).
Lu et al., "The PTEN/MMAC1/TEP tumor suppressor gene decreases cell growth and induces apoptosis and anoikis in breast cancer cells," Oncogene 18(50):7034-7045 (1999).
Lynch et al., "Novel Agents in the Treatment of Lung Cancer: Fourth Cambridge Conference," Clin. Cancer Res. 13(15 Suppl.):4583s-4588s (2007).
Lynch et al., "Summary statement novel agents in the treatment of lung cancer: Fifth Cambridge Conference assessing opportunities for combination therapy," J. Thorac. Oncol. 3(6 Suppl 2):S107-S112 (2008).
Lynch, "Molecular Staging of NSCLC: 2006," EJC (Suppl 4):24-25 Abstr. S55 (2006).
Ma et al., "PIK3CA as an oncogene in cervical cancer," Oncogene 19(23):2739-2744 (2000).

Macrinici and Romond, "Clinical updates on EGFR/HER targeted agents in early-stage breast cancer," Clin. Breast Cancer 10 Suppl 1:E38-E46 (2010).
Maehama et al., "A sensitive assay for phosphoinositide phosphatases," Anal. Biochem. 279(2):248-250 (2000).
Maehama et al., "PTEN and myotubularin: novel phosphoinositide phosphatases," Annu. Rev. Biochem. 70:247-279 (2001).
Maehama, "PTEN: its deregulation and tumorigenesis," Biol. Pharm. Bull. 30(9):1624-1627 (2007).
Mallon et al., "Antitumor efficacy of PKI-587, a highly potent dual PI3K/mTOR kinase inhibitor," Clin. Cancer Res. 17(10):3193-3203 (2011) (Epub Feb. 15, 2011).
Man et al., "New and established targets for the treatment of breast cancer," Adv. Breast Cancer 7(3):10-13 (2010).
Mantel and Haenszel, "Statistical aspects of the analysis of data from retrospective studies of disease," J. Natl. Cancer Inst. 22(4):719-748 (1959).
Martinez-Garcia et al., "Tyrosine Kinase Inhibitors in Breast Cancer: Present Status and Perspectives," Cancer Chemother. Rev. 186-194 (2010).
Mauriz and Gonzalez-Gallego, "Antiangiogenic drugs: current knowledge and new approaches to cancer therapy," J. Pharm. Sci. 97(10):4129-4154 (2008).
Mayer, "Treatment of HER2-positive metastatic breast cancer following initial progression," Clin. Breast Cancer 9 Suppl 2:S50-S57 (2009).
McDermott et al., "Acquired resistance of non-small cell lung cancer cells to MET kinase inhibition is mediated by a switch to epidermal growth factor receptor dependency," Cancer Res. 70(4):1625-1634 (2010) (Epub Feb. 2, 2010).
McDermott et al., "High-throughput lung cancer cell line screening for genotype-correlated sensitivity to an EGFR kinase inhibitor," Methods Enzymol. 438:331-341 (2008).
McDermott et al., "Identification of genotype-correlated sensitivity to selective kinase inhibitors by using high-throughput tumor cell line profiling," Proc. Natl. Acad. Sci. U.S.A. 104(50):19936-19941 (2007) (Epub Dec. 6, 2007).
Mehta and Osipo, "Trastuzumab resistance: role for Notch signaling," ScientificWorldJournal 9:1438-1448 (2009).
Mendelsohn and Baselga, "The EGF receptor family as targets for cancer therapy," Oncogene 19(56):6550-6565 (2000).
Mendoza, "Targeted therapies in the treatment of advanced non-small-cell lung cancer: update," Klin.Onkol. 22(4):131-138 (2009).
Meng et al., "MicroRNA-21 regulates expression of the PTEN tumor suppressor gene in human hepatocellular cancer," Gastroenterology 133(2):647-658 (2007) (Epub May 21, 2007).
Metro and Cappuzzo, "New targeted therapies for non-small-cell lung cancer," Therapy 6(3):335-350 (2009).
Metzger-Filho et al., "Management of metastatic HER2-positive breast cancer progression after adjuvant trastuzumab therapy—current evidence and future trends," Expert Opin. Investig. Drugs 19 Suppl 1:S31-S39 (2010).
Metzger-Filho et al., "Molecular targeted therapy in prevalent tumors: learning from the past and future perspectives," Current Clin. Pharmacol. 5(3):166-177 (2010).
Minkovsky and Berezov, "BIBW-2992, a dual receptor tyrosine kinase inhibitor for the treatment of solid tumors," Curr. Opin. Investig. Drugs 9(12):1336-1346 (2008).
Mitsudomi et al., "Biological and clinical implications of EGFR mutations in lung cancer," Int. J. Clin. Oncol. 11(3):190-198 (2006).
Moasser, "Targeting the function of the HER2 oncogene in human cancer therapeutics," Oncogene 26(46):6577-6592 (2007) (Epub May 7, 2007).
Morabito et al., "Methodological Issues of Clinical Research with EGFR Inhibitors," Curr. Cancer Ther. Rev. 3(4):292-302 (2007).
Moreno-Aspitia and Perez, "Treatment options for breast cancer resistant to anthracycline and taxane," Mayo Clin. Proc. 84(6):533-545 (2009).
Morozova et al., "System-level analysis of neuroblastoma tumor-initiating cells implicates AURKB as a novel drug target for neuroblastoma," Clin. Cancer Res. 16(18):4572-4582 (2010) (Epub Jul. 22, 2010).

(56) References Cited

OTHER PUBLICATIONS

Morris and Hudis, "Personalizing therapy for metastatic breast cancer," Expert Rev. Anticancer Ther. 9(9):1223-1226 (2009).
Morrow et al., "Recent advances in systemic therapy: Advances in systemic therapy for HER2-positive metastatic breast cancer," Breast Cancer Res. 11(4):207 (2009) (Epub Jul. 15, 2009).
Mukai, "Targeted therapy in breast cancer: current status and future directions," Jpn. J. Clin. Oncol. 40(8):711-716 (2010) (Epub Apr. 8, 2010).
Mukai, "Treatment strategy for HER2-positive breast cancer," Int. J. Clin. Oncol. 15(4):335-340 (2010) (Epub Jul. 15, 2010).
Mukherji and Spicer, "Second-generation epidermal growth factor tyrosine kinase inhibitors in non-small cell lung cancer," Expert Opin. Investig. Drugs 18(3):293-301 (2009).
Mullard, "2010 in Reflection," Nat. Rev. Drug Discov. 10:7-9 (2011).
Munagala et al., "Promising molecular targeted therapies in breast cancer," Indian J. Pharmacol. 43(3):236-245 (2011).
Mundhenke et al., "Significance of Tyrosine Kinase Inhibitors in the Treatment of Metastatic Breast Cancer," Breast Care (Basel) 4(6):373-378 (2009) (Epub Nov. 16, 2009).
Murphy and Fornier, "HER2-positive breast cancer: beyond trastuzumab," Oncology (Williston Park) 24(5):410-415 (2010).
Muthuswamy, "Trastuzumab resistance: all roads lead to SRC," Nat. Med. 17(4):416-418 (2011).
Nagata et al., "PTEN activation contributes to tumor inhibition by trastuzumab, and loss of PTEN predicts trastuzumab resistance in patients," Cancer Cell vol. 6(2):117-127 (2004).
Nahta and O'Regan, "Evolving strategies for overcoming resistance to HER2-directed therapy: targeting the PI3K/Akt/mTOR pathway," Clin. Breast Cancer 10 Suppl 3:S72-S78 (2010).
Natoli et al., "Tyrosine kinase inhibitors," Curr. Cancer Drug Targets 10(5):462-483 (2010).
Nguyen et al., "Acquired resistance to epidermal growth factor receptor tyrosine kinase inhibitors in non-small-cell lung cancers dependent on the epidermal growth factor receptor pathway," Clin. Lung Cancer 10(4):281-289 (2009).
Nicholson et al., "EGFR and cancer prognosis," Eur. J. Cancer 37 Suppl 4:S9-S15 (2001).
Nielsen et al., "HER2-targeted therapy in breast cancer. Monoclonal antibodies and tyrosine kinase inhibitors," Cancer Treat Rev. 35(2):121-136 (2009) (Epub Nov. 12, 2008).
Nitz, "Perspectives: Other ErbB2-Targeted Therapies," Breast Care (Basel) 5(s1):25-27 (2010) (Epub Apr. 26, 2010).
O'Brien et al., "Activated phosphoinositide 3-kinase/AKT signaling confers resistance to trastuzumab but not lapatinib," Mol. Cancer Ther. 9(6):1489-1502 (2010) (Epub May 25, 2010).
Ocaña and Amir, "Irreversible pan-ErbB tyrosine kinase inhibitors and breast cancer: current status and future directions," Cancer Treat. Rev. 35(8):685-691 (2009) (Epub Sep. 4, 2009).
Ocaña et al., "New Targeted Therapies in Head and Neck Cancer," Cancer Chemo. Rev. 4:35-43 (2009).
Ocaña et al., "Novel tyrosine kinase inhibitors in the treatment of cancer," Curr. Drug Targets 10(6):575-576 (2009).
Ocaña et al., "Preclinical development of molecular-targeted agents for cancer," Nat. Rev. Clin. Oncol. 8:200-209 (2011).
Oh et al., "Detection of epidermal growth factor receptor in the serum of patients with cervical carcinoma," Clin. Cancer Res. 6(12):4760-4763 (2000).
O'Hare et al., "Bcr-Abl kinase domain mutations and the unsettled problem of Bcr-AblT315I: looking into the future of controlling drug resistance in chronic myeloid leukemia," Clin. Lymphoma Myeloma 7 Suppl 3:S120-S130 (2007).
Omuro et al., "Lessons learned in the development of targeted therapy for malignant gliomas," Mol. Cancer Ther. 6(7):1909-1919 (2007).
O'Neil et al., (ed.). The Merck Index—An Encyclopedia of Chemicals, Drugs, and Biologicals. 13th Edition, Whitehouse Station, NJ: Merck and Co., Inc., 2001., p. 1454-1455.

Pal et al., "Targeted therapies for non-small cell lung cancer: an evolving landscape," Mol. Cancer Ther. 9(7):1931-1944 (2010) (Epub Jun. 22, 2010).
Pallis et al., "Targeted therapies in the treatment of advanced/metastatic NSCLC," Eur. J. Cancer 45(14):2473-2487 (2009).
Pantuck et al., "Prognostic relevance of the mTOR pathway in renal cell carcinoma: implications for molecular patient selection for targeted therapy," Cancer 109(11):2257-2267 (2007).
Pao and Chmielecki, "Rational, biologically based treatment of EGFR-mutant non-small-cell lung cancer," Nat. Rev. Cancer 10(11):760-774 (2010) (Epub Oct. 22, 2010).
Pao, "Defining clinically relevant molecular subsets of lung cancer," Cancer Chemother. Pharmacol. 58(Suppl 1):s11-s15 (2006).
Paridaens et al., "Neratinib (HKI-272), an irreversible pan-ErbB receptor tyrosine kinase inhibitor: Phase 2 results in patients with ErbB2+ advanced breast cancer," Ann. Oncol. 20(Suppl 2):ii61-ii62 Abstr. 186P (2009).
Pegram et al., "Expert roundtable: emerging questions in ErbB2-positive breast cancer; Feb. 22, 2007," Clin. Breast Cancer 8(Suppl 3):S131-S141 (2008).
Perez et al., "Updated Results of the Combined Analysis of NCCTG N9831 and NSABP B-31 Adjuvant Chemotherapy With/Without Trastuzumab in Patients with HER2-Positive Breast Cancer," J. Clin. Oncol. ASCO Annual Meeting Proc. 25(18S):512 (2007).
Pérez-Soler, "Individualized therapy in non-small-cell lung cancer: future versus current clinical practice," Oncogene 28(Suppl 1):S38-S45 (2009).
Pérez-Tenorio et al., "PIK3CA mutations and PTEN loss correlate with similar prognostic factors and are not mutually exclusive in breast cancer," Clin. Cancer Res. 13(12):3577-3584 (2007).
Perren et al., "Immunohistochemical evidence of loss of PTEN expression in primary ductal adenocarcinomas of the breast," Am. J. Pathol. 155(4):1253-1260 (1999).
Petter et al., "A novel small-molecule drug platform to silence cancer targets—application to the panErbB kinases," In: Proceedings of the 100th Annual Meeting of the American Association for Cancer Research; Apr. 18-22, 2009; Denver, CO. Abstr. 3746 (2009).
Piccart et al., "Beyond trastuzumab: new anti-HER2 agents," Breast 20(Suppl 1):S1-S2 Abstr. S02 (2011).
Piccart, "Circumventing de novo and acquired resistance to trastuzumab: new hope for the care of ErbB2-positive breast cancer," Clin. Breast Cancer 8(Suppl 3):S100-S113 (2008).
Plati et al., "Dysregulation of apoptotic signaling in cancer: molecular mechanisms and therapeutic opportunities," J. Cell. Biochem. 104(4):1124-1149 (2008).
Plosker and Keam, "Trastuzumab: a review of its use in the management of HER2-positive metastatic and early-stage breast cancer," Drugs 66(4):449-475 (2006).
Ponz-Sarvisé et al., "Epidermal growth factor receptor inhibitors in colorectal cancer treatment: what's new?" World J. Gastroenterol. 13(44):5877-5887 (2007).
Potashman and Duggan, "Covalent modifiers: an orthogonal approach to drug design," J. Med. Chem. 52(5):1231-1246 (2009).
Rabindran, "Antitumor activity of HER-2 inhibitors," Cancer Lett. 227(1):9-23 (2005) (Epub Dec. 15, 2004).
Rana and Swaby, "Targeted Therapies for HER2 Breast Cancer: A View of the Landscape," Curr. Breast Cancer Rep. 3:55-62 (2011).
Ranganathan and Muneer, "Highlights from: The 24th Annual Meeting of the American Association for Cancer Research; Los Angeles, CA; Apr. 14-18, 2007," Clin. Lung Cancer 8(6):359-363 (2007).
Ray et al., "Lung cancer therapeutics that target signaling pathways: an update," Expert Rev. Respir. Med. 4(5):631-645 (2010).
Ray et al., "The role of EGFR inhibition in the treatment of non-small cell lung cancer," Oncologist 14(11):1116-1130 (2009) (Epub Nov. 5, 2009).
Redon et al., "A simple specific pattern of chromosomal aberrations at early stages of head and neck squamous cell carcinomas: PIK3CA but not p63 gene as a likely target of 3q26-qter gains," Cancer Res. 61(10):4122-4129 (2001).
Rewcastle et al., "Synthesis of 4-(phenylamino)pyrimidine derivatives as ATP-competitive protein inhibitors with potential for cancer chemotherapy," Curr. Org. Chem. 4(7):679-706 (2000).

(56) References Cited

OTHER PUBLICATIONS

Rexer et al., "Overcoming resistance to tyrosine kinase inhibitors: lessons learned from cancer cells treated with EGFR antagonists," Cell Cycle 8(1):18-22 (2009) (Epub Jan. 30, 2009).
Riely et al., "Update on epidermal growth factor receptor mutations in non-small cell lung cancer," Clin. Cancer Res. 12(24):7232-7241 (2006).
Riely, "Second-generation epidermal growth factor receptor tyrosine kinase inhibitors in non-small cell lung cancer," J. Thorac. Oncol. 3(6 Suppl 2):S146-S149 (2008).
Rosell et al., "Age-related genetic abnormalities: the Achilles' heel for customizing therapy in elderly lung cancer patients," Personalized Medicine 4(1):59-72 (2007).
Rosell et al., "Screening for epidermal growth factor receptor mutations in lung cancer," N. Engl. J. Med. 361(10):958-967 (2009) (Epub Aug. 19, 2009).
Rosell et al., "Treatment of non-small-cell lung cancer and pharmacogenomics: where we are and where we are going," Curr. Opin. Oncol. 18(2):135-143 (2006).
Rosen et al., "Targeting signal transduction pathways in metastatic breast cancer: a comprehensive review," Oncologist 15(3):216-235 (2010) (Epub Mar. 3, 2010).
Ross et al., "The HER-2 receptor and breast cancer: ten years of targeted anti-HER-2 therapy and personalized medicine," Oncologist 14:320-368 (2009).
Rotella, "Medicinal Chemistry—XXth International Symposium. Lead finding strategies and kinase selectivity," IDrugs 11(11):774-778 (2008).
Roukos, "Trastuzumab and beyond: sequencing cancer genomes and predicting molecular networks," Pharmacogenomics J. 11(2):81-92 (2011) (Epub Oct. 26, 2010).
Roy and Perez, "Beyond trastuzumab: small molecule tyrosine kinase inhibitors in HER-2-positive breast cancer," Oncologist 14(11):1061-1069 (2009) (Epub Nov. 3, 2009).
Rubin et al., "10q23.3 loss of heterozygosity is higher in lymph node-positive (pT2-3,N+) versus lymph node-negative (pT2-3,N0) prostate cancer," Hum. Pathol. 31(4):504-508 (2000).
Rudloff and Samuels, "A growing family: adding mutated Erbb4 as a novel cancer target," Cell Cycle. 9(8):1487-1503 (2010) (Epub Apr. 15, 2010).
Saal et al., "PIK3CA mutations correlate with hormone receptors, node metastasis, and ERBB2, and are mutually exclusive with PTEN loss in human breast carcinoma," Cancer Res. 65(7):2554-2559 (2005).
Salvesen et al., "Integrated genomic profiling of endometrial carcinoma associates aggressive tumors with indicators of PI3 kinase activation," Proc. Natl. Acad. Sci. U.S.A. 106(12):4834-4839 (2009) (Epub Mar. 4, 2009).
Samuels and Ericson, "Oncogenic PI3K and its role in cancer," Curr. Opin. Oncol. 18(1):77-82 (2006).
Sanchez-Martin and Pandiella, "Differential action of ErbB kinase inhibitors on receptor oligomerization," EJC Suppl. 8:107 Abstr. 337 (2010).
Santarpia et al., "Tyrosine kinase inhibitors for non-small-cell lung cancer: finding patients who will be responsive," Expert Rev. Respir. Med. (3):413-424 (2011).
Sartore-Bianchi et al., "Rationale and clinical results of multi-target treatments in oncology," Int. J. Biol. Markers 22(1 Suppl 4):S77-S87 (2007).
Sathornsumetee et al., "Malignant glioma drug discovery—targeting protein kinases," Expert Opin. Drug Discov. 2(1):1-17 (2007).
Sattler et al., "EGFR-targeted therapeutics: focus on SCCHN and NSCLC," ScientificWorldJournal 8:909-919 (2008).
Saura et al., "Safety of Neratinib (HKI-272) in Combination with Capecitabine in Patients with Solid Tumors: A Phase 1/2 Study," Cancer Res. 69(24 Suppl) Abstr. 5108 (2009).
Saura et al., "The safety of Neratinib (HKI-272) in Combination with Capecitabine in Patients with Solid Tumors: A Phase 1/2 Study," Ann. Oncol. 21(Suppl 4):iv63 Abstr. 147P (2010).
Scaltriti et al., "Expression of p95HER2, a truncated form of the HER2 receptor, and response to anti-HER2 therapies in breast cancer," J. Natl. Cancer Inst. 99(8):628-638 (2007).
Schiller et al., "Comparison of four chemotherapy regimens for advanced non-small-cell lung cancer," N. Engl. J. Med. 346(2):92-98 (2002).
Scott and Salgia, "Biomarkers in lung cancer: from early detection to novel therapeutics and decision making," Biomark. Med. 2(6):577-586 (2008).
Sebastian et al., "The complexity of targeting EGFR signalling in cancer: from expression to turnover," Biochim. Biophys. Acta. 1766(1):120-139 (2006) (Epub Jun. 23, 2006).
Sequist and Dziadziuszko, "Update on epidermal growth factor receptor inhibitor development in lung cancer," J. Thorac. Oncol. 1(7):740-743 (2006).
Sequist et al., "Neratinib, an irreversible pan-ErbB receptor tyrosine kinase inhibitor: results of a phase II trial in patients with advanced non-small-cell lung cancer," J. Clin. Oncol. 28(18):3076-3083 (2010) (Epub May 17, 2010).
Sequist, "Second-generation epidermal growth factor receptor tyrosine kinase inhibitors in non-small cell lung cancer," Oncologist 12(3):325-330 (2007).
Settleman and Kurie, "Drugging the bad "AKT-TOR" to overcome TKI-resistant lung cancer," Cancer Cell 12(1):6-8 (2007).
Seyhan et al., "A genome-wide RNAi screen identifies novel targets of neratinib sensitivity leading to neratinib and paclitaxel combination drug treatments," Mol. Biosyst. 7(6):1974-1989 (2011) (Epub Apr. 12, 2011).
Sharma and Jayanth, "Neratinib, an irreversible erbB receptor tyrosine Kinase inhibitor, in patients with advanced erbB2-positive breast cancer," [commentary] Adv. Breast Cancer 7(1):21 (2010).
Sharma and Settleman, "Oncogene addiction: setting the stage for molecularly targeted cancer therapy," Genes Dev. 21(24):3214-3231 (2007).
Sharma et al., "Epidermal growth factor receptor mutations in lung cancer," Nat. Rev. Cancer 7(3):169-181 (2007).
Sharma et al., "Receptor tyrosine kinase inhibitors as potent weapons in war against cancers," Curr. Pharm. Des. 15(7):758-776 (2009).
Shayesteh et al., "PIK3CA is implicated as an oncogene in ovarian cancer," Nat. Genet. 21(1):99-102 (1999).
Shimamura and Shapiro, "Heat shock protein 90 inhibition in lung cancer," J. Thorac. Oncol. 3(6 Suppl 2):S152-S159 (2008).
Shimamura et al., "Hsp90 inhibition suppresses mutant EGFR-T790M signaling and overcomes kinase inhibitor resistance," Cancer Res. 68(14):5827-5838 (2008).
Shimamura et al., "On-small-cell lung cancer and Ba/F3 transformed cells harboring the ERBB2 G776insV_G/C mutation are sensitive to the dual-specific epidermal growth factor receptor and ERBB2 inhibitor HKI-272," Cancer Res. 66(13):6487-6491 (2006).
Sibilia et al., "The epidermal growth factor receptor: from development to tumorigenesis," Differentiation 75(9):770-787 (2007).
Sigal, "Basic science for the clinician 48: tyrosine kinases in disease: the potential for inhibitors in the treatment of immunologic diseases," J. Clin. Rheumatol. 14(1):45-48 (2008).
Simon et al., "By 1023/SK&F 96022: biochemistry of a novel (H+ + K+)-ATPase inhibitor," Biochem Pharmacol. 39(11):1799-1806 (1990).
Singh et al., "Targeted covalent drugs of the kinase family," Curr. Opin. Chem. Biol. 14(4):475-480 (2010) (Epub Jul. 6, 2010).
Singh et al., "The resurgence of covalent drugs," Nat. Rev. Drug Discov. 10(4):307-317 (2011).
Slamon et al., "BCIRG 006: 2nd interim analysis phase III randomized trial comparing doxorubicin and cyclophosphamide followed by docetaxel (AC-T) with doxorubicin and cyclophosphamide followed by docetaxel and trastuzumab (AC-TH) with docetaxel, carboplatin and trastuzumab (TCH) in Her2neu positive early breast cancer patients," in: *San Antonio Breast Cancer Symposium*; 2006 [abstract 52].
Slamon et al., "Human breast cancer: correlation of relapse and survival with amplification of the HER-2/neu oncogene," Science 235(4785):177-182 (1987).

(56) References Cited

OTHER PUBLICATIONS

Smith et al., "2-year follow-up of trastuzumab after adjuvant chemotherapy in HER2-positive breast cancer: a randomised controlled trial." Lancet 369(9555):29-36 (2007).
Solca et al., "Beyond Trastuzumab: Second-Generation Targeted Therapies for HER-2-Positive Breast Cancer," Drugs for HER-2-positive Breast Cancer, Milestones in Drug Therapy, 2011 p. 91-107 (2011).
Specht and Gralow, "Neoadjuvant chemotherapy for locally advanced breast cancer," Semin. Radiat. Oncol. 9(4):222-228 (2009).
Spector et al., "Small Molecule HER-2 Tyrosine Kinase Inhibitors," Breast Cancer Res. 9(2):205 (2007).
Spector, "Treatment of metastatic ErbB2-positive breast cancer: options after progression on trastuzumab," Clin. Breast Cancer 8 Suppl 3:S94-S99 (2008).
Spicer and Rudman, "EGFR inhibitors in non-small cell lung cancer (NSCLC): the emerging role of the dual irreversible EGFR/HER2 inhibitor BIBW 2992," Target Oncol. 5(4):245-255 (2010) (Epub Jun. 24, 2010).
Srivastava et al., "Synthesis and structure-activity relationships of potent antitumor active quinoline and naphthyridine derivatives," Anticancer Agents Med. Chem. 7(6):685-709 (2007).
Staroslawska et al. (Dec. 2010). Safety and Efficacy of Neratinib (HKI-272) Plus Vinorelbine in the Treatment of Patients With ErbB2+ Metastatic Breast Cancer Pretreated With Anti-Her2 Therapy. Poster presented at teh 33rd Annual San Antonio Breast Cancer Symposium, San Antonio, Texas.
Stebbing et al., "Lemur tyrosine kinase-3 (LMTK3) in cancer and evolution," Oncotarget 2(6):428-429 (2011).
Steins et al., "Targeting the epidermal growth factor receptor in non-small cell lung cancer," Onkologie 33(12):704-709 (2010) (Epub Nov. 26, 2010).
Stemke-Hale et al., "An integrative genomic and proteomic analysis of PIK3CA, PTEN, and AKT mutations in breast cancer," Cancer Res. 68(15):6084-6091 (2008).
Stockler et al., "Chemotherapy for advanced breast cancer—how long should it continue?" Breast Cancer Res. Treat. 81(Suppl. 1):S49-S52 (2003).
Stokoe et al., "Dual role of phosphatidylinositol-3,4,5-trisphosphate in the activation of protein kinase B," Science 277(5325):567-570 (1997).
Swaby et al., "Neratinib in combination with trastuzumab for the treatment of advanced breast cancer: A phase I/II study," J. Clin. Oncol. 27:15s(suppl; abstr 1004) (2009).
Tagliabue et al., "HER2 as a target for breast cancer therapy," Expert Opin. Biol. Ther. 10(5):711-724 (2010).
Takada, "API Form Screening and Selection in Drug Discovery Stage," Pharm Stage 6(10):20-25 (2007). [English Translation Not Available].
Tjin Tham Sjin et al., "Design of a novel covalent EGFR mutant-selective inhibitor," EJC Suppl. 8(7):31 Abstr. 73 (2010).
Toffoli et al., "Pharmacology of epidermal growth factor inhibitors," Int. J. Biol. Markers 22(1 Suppl 4):S24-S39 (2007).
Tolaney and Krop, "Mechanisms of trastuzumab resistance in breast cancer," Anticancer Agents Med. Chem. 9(3):348-355 (2009).
Tolaney et al., "HER2-Positive Breast Cancer," JCOM 14(7):395-403 (2007).
Tomillero and Moral, "Gateways to Clinical Trials," Methods Find. Exp. Clin. Pharmacol. 31(3):183-226 (2009).
Tomillero and Moral, "Gateways to Clinical Trials," Methods Find. Exp. Clin. Pharmacol. 31(10):661-700 (2009).
Tookman and Roylance, "New Drugs for Breast Cancer," Br. Med. Bull. 96:111-129 (2010) (Epub Sep. 23, 2010).
Torres and Harris, "Polycystic kidney disease: genes, proteins, animal models, disease mechanisms and therapeutic opportunities," J. Intern. Med. 261(1):17-31 (2007).
Traxler, "Tyrosine kinase inhibitors in cancer treatment (Part II)," Exp. Opin. Ther. Patents 8(12):1599-1625 (1998).
Tsou et al., "Optimization of 6,7-Disubstituted-4-(Arylamino)Quinoline-3-Carbonitriles as Orally Active, Irreversible Inhibitors of Human Epidermal Growth Factor Receptor-2 Kinase Activity," J. Med. Chem. 48(4):1107-1131 (2005).
Tsou, "American Chemical Society—226th National Meeting. Novel Substituted 4-Anilinoquinoline-3-carbonitriles as orally active, irreversible binding inhibitors of HER-2 Kinase," (abstr. 14) 2003.
Untch, "Targeted Therapy for Early and Locally Advanced Breast Cancer," Breast Care (Basel) 5(3):144-152 (2010) (Epub Jun. 16, 2010).
Upeslacis, Janis, Meeting At Mcgill University, Canada, Evolution of Kinase Inhibitors At Wyeth, Oct. 16, 2002.
Van Arnum, "Evaluating late-stage pipelines and potential: will 2011 be a more promising year for new molecular entities? A review of Big Pharma's late-stage pipeline shows what might lie ahead." Pharmaceutical Technology 35.2 (2011): 52+. Expanded Academic ASAP. Web. Jul. 18, 2011.
Vasudevan et al., "AKT-independent signaling downstream of oncogenic PIK3CA mutations in human cancer," Cancer Cell 16(1):21-32 (2009).
Vazquez et al., "HER2-Positive Breast Cancer: Analysis of Efficacy in Different Groups," Cancer Chemother. Rev. 4(4):224-240 (2009).
Vivanco and Mellinghoff, "Epidermal growth factor receptor inhibitors in oncology," Curr. Opin. Oncol. 22(6):573-578 (2010).
Von Eyben, "Epidermal growth factor receptor inhibition and non-small cell lung cancer," Crit. Rev. Clin. Lab. Sci. 43(4):291-323 (2006).
Vora et al., "Novel Therapeutics in Breast Cancer—Looking to the Future," Update on Cancer Therapeutics 3:189-205 (2009).
Wagner and Kaufmann, "Prospects for the Use of ATR Inhibitors to Treat Cancer," Pharmaceuticals 3:1311-1334 (2010).
Wang et al., "Characterization of HKI-272 covalent binding to human serum albumin," Drug Metab. Dispos. 38(7):1083-1093 (2010) (Epub Apr. 16, 2010).
Weber, "Toward a molecular classification of cancer," Toxicology Dec. 5, 2010;278(2):195-198 (2010) (Epub Oct. 24, 2009).
Wen and Drappatz, "Novel therapies for meningiomas," Expert Rev. Neurother. 6(10):1447-1464 (2006).
Wheatley-Price and Shepherd, "Epidermal growth factor receptor inhibitors in the treatment of lung cancer: reality and hopes," Curr. Opin. Oncol. 20(2):162-175 (2008).
Whenham et al., "HER2-positive breast cancer: from trastuzumab to innovatory anti-HER2 strategies," Clin. Breast Cancer 8(1):38-49 (2008).
Widakowich et al., "HER-2 positive breast cancer: what else beyond trastuzumab-based therapy?" Anticancer Agents Med. Chem. 8(5):488-496 (2008).
Widakowich et al., "Molecular targeted therapies in breast cancer: where are we now?" Int. J. Biochem. Cell. Biol. 2007;39(7-8):1375-1387 (2007) (Epub May 4, 2007).
Wissner et al., "Dual irreversible kinase inhibitors: quinazoline-based inhibitors incorporating two independent reactive centers with each targeting different cysteine residues in the kinase domains of EGFR and VEGFR-2," Bioorg. Med. Chem. 15(11):3635-4368 (2007) (Epub Mar. 23, 2007).
Woenckhaus et al., "Prognostic value of PIK3CA and phosphorylated AKT expression in ovarian cancer," Virchows Arch. 450(4):387-395 (2007) (Epub Feb. 15, 2007).
Wondrak, "Redox-directed cancer therapeutics: molecular mechanisms and opportunities," Antioxid. Redox Signal. 11(12):3013-3069 (2009).
Wong et al., "A phase I study with neratinib (HKI-272), an irreversible pan ErbB receptor tyrosine kinase inhibitor, in patients with solid tumors," Clin. Cancer Res. 15(7):2552-2558 (2009) (Epub Mar. 24, 2009).
Wong et al., "HKI-272, an irreversible pan ErbB receptor tyrosine kinase inhibitory: Preliminary phase 1 results in patients with solid tumors," J. Clin. Oncol. 24(18S):125s Abstr. 3018 (2006).
Wong, "Searching for a magic bullet in NSCLC: the role of epidermal growth factor receptor mutations and tyrosine kinase inhibitors," Lung Cancer 60(Suppl 2):S10-S18 (2008).
World Health Organization (2008). Fact Sheet—Cancer, No. 297, 2008. Retrieved from http://www.who.int/mediacentre/factsheets/fs297/en/.

(56) References Cited

OTHER PUBLICATIONS

World Health Organization (2008). *World Health Statistics*, 2008. Retrieved from http://www.who.int/gho/publications/world_health_statistics/EN_WHS08_Full.pdf?ua=1.

Written Opinion of the International Searching Authority for International Application No. PCT/US2009/047643 dated Dec. 17, 2010.

Wu et al., "Design and synthesis of tetrahydropyridothieno[2,3-d]pyrimidine scaffold based epidermal growth factor receptor (EGFR) kinase inhibitors: the role of side chain chirality and Michael acceptor group for maximal potency," J. Med. Chem. 53(20):7316-7326 (2010).

Wu et al., "Somatic mutation and gain of copy number of PIK3CA in human breast cancer," Breast Cancer Res. 7(5):R609-R616 (2005) (Epub May 31, 2005).

Wu et al., "TAK-285, a Novel HER2/EGFR Inhibitor, Penetrates the CNS in Rats with an Intact Blood Brain Barrier (BBB),"Cancer Res. 69(24 Suppl): Abstr. 5098 (2009).

Wu et al., "Uncommon mutation, but common amplifications, of the PIK3CA gene in thyroid tumors," J. Clin. Endocrinol. Metab. 90(8):4688-4693 (2005) (Epub May 31, 2005).

Wykosky et al., "Therapeutic targeting of epidermal growth factor receptor in human cancer: successes and limitations," Chin. J. Cancer 30(1):5-12 (2011).

Xu et al., "Acquired resistance of lung adenocarcinoma to EGFR-tyrosine kinase inhibitors gefitinib and erlotinib," Cancer Biol. Ther. 9(8):572-582 (2010) (Epub Apr. 26, 2010).

Yoshida et al., "Targeting epidermal growth factor receptor: central signaling kinase in lung cancer," Biochem. Pharmacol. 80(5):613-623 (2010) (Epub May 24, 2010).

Yuan and Cantley, "PI3K pathway alterations in cancer: variations on a theme," Oncogene 27(41):5497-5510 (2008).

Yun et al., "The T790M mutation in EGFR kinase causes drug resistance by increasing the affinity for ATP," Proc. Natl. Acad. Sci. U.S.A. 105(6):2070-2075 (2008) (Epub Jan. 28, 2008).

Yuza et al., "Allele-dependent variation in the relative cellular potency of distinct EGFR inhibitors," Cancer Biol. Ther. 6(5):661-667 (2007) (Epub Feb. 13, 2007).

Zagrekova et al., "Drug Treatment of Breast Cancer," Rossijskij Medicinskij Zhurnal 14:605 (2002). (English Translation Not Available).

Zahnow, "ErbB receptors and their ligands in the breast," Expert Rev. Mol. Med. 8(23):1-21 (2006).

Zhang et al. Xenograft Models of Breast Cancer: the Link between Characteristics of Biomarker Expression and the Anti-tumor Effect of the Representative Therapies [abstract]. In: Proceedings of the 101st Annual Meeting of the American Association for Cancer Research; Apr. 17-21, 2010; Washington, DC. Philadelphia (PA): AACR; Cancer Res 2010;70(8 Suppl):Abstract nr 647.

Zhang et al., "Advances in preclinical small molecules for the treatment of NSCLC," Expert Opin. Ther. Pat. 19(6):731-751 (2009).

Zhao et al., "Neratinib Reverses ATP-Binding Cassette Bl-Mediaed Chemotherapeutic Drug Resistance in Vitro, in Vivo, and Ex-Vivo," Mol. Pharmacal. 82: 47-58 (2012).

Zhou et al., "Activation of the PTEN/Mtor/STAT3 Pathway in Breast Cancer Stem-Like Cells Is Required for Viability and Maintenance," Proc. Natl. Acad. Sci. U.S.A. 104:16158-16163 (2007).

Zhou et al., "Novel Mutant-Selective EGFR Kinase Inhibitors Against EGFR T790M," Nature 462(7276):1070-1074 (2009).

Zhang et. al., "Targeting cancer with small molecule kinase inhibitors," Nature, 9: 28-39 (2009).

\* cited by examiner

ANTINEOPLASTIC COMBINATIONS OF 4-ANILINO-3-CYANOQUINOLINES AND CAPECITABINE

CROSS REFERENCE TO RELATED APPLICATIONS

This application is a continuation of U.S. patent application Ser. No 12/534,895, filed Aug. 4, 2009, which claims the benefit under U.S.C. §119(e) to U.S. Provisional Application Ser. No. 61/085,913, filed Aug. 4, 2008 and U.S. Provisional Application Ser. No. 61/172,466, filed Apr. 24, 2009, the disclosure of each of which is incorporated by reference herein in its entirety.

BACKGROUND OF THE INVENTION

Breast cancer is the most frequently diagnosed malignancy in women and one of the top two causes of cancer-related deaths in women worldwide [Parkin D M, Fernandez L M. Use of statistics to assess the global burden of breast cancer. *Breast Journal*. January-February 2006; 12 Suppl 1:S70-80]. The incidence of breast cancer is estimated to reach 5 million women in the next decade.

Among women with primary breast cancer, 40 to 50% will develop metastatic disease, which despite active cytotoxic chemotherapy and newer biologic agents remains incurable [Smith I. Goals of treatment for patients with metastatic breast cancer. *Seminars in Oncology*. February 2006; 33(1 Suppl 2):S2-5]. As a result, treatment is aimed at palliation and improved quality of life, inhibition of disease progression and improvement in survival time.

The erythroblastic leukemia viral oncogene homolog (erb) family of tyrosine kinase inhibitors (TKIs) consists of 4 members: erbB-1 (EGFR [epidermal growth factor receptor]), erbB-2 (HER2, neu), erbB-3 (HER3) and erbB-4 (HER4). The erbB family of receptors is involved in cell proliferation, tumorigenesis, and metastasis and is abnormally expressed in multiple tumor types. The oncogenic role of erbB-2 has been most extensively documented in breast cancer, where gene amplification (as measured by positive fluorescence in situ hybridization [FISH]) or overexpression (as measured by immunohistochemistry [IHC] 3+) occurs in 25%-30% of breast cancers. Subjects with erbB-2-overexpressing breast cancers have been associated with more aggressive disease and poorer prognosis than for subjects whose tumors do not overexpress erbB-2 [Pegram M D, et al., The molecular and cellular biology of HER2/neu gene amplification/overexpression and the clinical development of herceptin (trastuzumab) therapy for breast cancer. *Cancer Treatment & Research*. 2000; 103:57 75].

Many different cytotoxic agents are currently available for the treatment of metastatic breast cancer (MBC), and multiple factors determine the choice of treatment. These include previous adjuvant therapy, tumor characteristics, subject characteristics, and subject preference. As anthracycline and taxanes are the most active cytotoxic agents in breast cancer, anthracycline/taxane-containing regimens are the mainstay of adjuvant therapy.

Capecitabine has been on the market since 1998, when it was the first oral chemotherapy approved by the FDA for the treatment of metastatic breast cancer [FDA. Prescribing Information for Xeloda® (capecitabine) U.S. Government; 2006]. Capecitabine (5'-deoxy-5-fluoro-N-[(pentyloxy)carboyl]-cytidine) is a fluoropyidine carbamate analog with anti-tumor activity. Capecitabine is used as monotherapy and in combination therapy regimens for the treatment and palliative management of various forms of cancer including colorectal and breast cancer. Despite its demonstrated clinical usefulness, there are a number of disadvantages associated with the use of capecitabine which can be dose-limiting and which may render patients unable to tolerate treatment using capecitabine. Adverse reactions commonly seen during systemic therapy using capecitabine, include diarrhea, stomatitis, nausea and vomiting, hand-and-foot syndrome, anemia, hyperbilirubinemia, dermatitis and alopecia. Other adverse effects associated with the systemic administration of capecitabine include constipation, abdominal pain, edema, decrease appetite, dyspnea, back pain, neutropenia, nail disorders, pyrexia, asthenia, fatigue, weakness, headache dizziness, anorexia, arthralgia, myaligia, neutropenic fever, cough, sore throat, leukopenia and thrombocytopenia.

The use of the antibody trastuzumab for breast cancer treatment has been described. However, breast cancer cells may become resistant to trastuzumab on the basis of extra-cellular domain (ECD) truncated erbB-2 receptor, that can no longer be recognized by the antibody [Xia, W. Truncated ErbB2 receptor (p95ErbB2) is regulated by heregulin through heterodimer formation with ErbB3 yet remains sensitive to the dual EGFR/ErbB2 kinase inhibitor GW572016. *Oncogene* 2004, 23:646-653], or because of coactivation of erbB-1 signaling [Rampaul, R S, et al, Clinical value of epidermal growth factor receptor expression in primary breast cancer. *Adv Anat Pathol* 2005, 12:271-273; Zaczek, A, et al., The diverse signaling network of EGFR, HER2, HER3 and HER4 tyrosine kinase receptors and the consequences for therapeutic approaches. *Histol Histopathol* 2005, 20:1005-1015].

What are needed are additional effective therapies for solid tumors and/or breast cancer.

SUMMARY OF THE INVENTION

In one aspect, a combination therapy for an Erb-1 overexpressing (amplified) and/or an Erb-2-overexpressing (amplified) neoplasm is provided. This combination therapy comprises a regimen involving the two anti-neoplastic agents HKI-272 (neratinib) and capecitabine.

In another aspect, a combination therapy for treatment of a solid tumor neoplasm in a subject is provided which includes administering HKI-272 and administering capecitabine.

In still another aspect, a combination therapy is useful for treatment of breast cancer.

In yet another aspect, the combination therapy is utilized for treatment of ErbB-2 positive metastatic or locally advanced breast cancer is provided. This combination therapy comprises delivering a combination of HKI-272 and capecitabine.

In yet a further aspect, a pharmaceutical pack for treating a neoplasm in one individual mammal is provided and includes (a) at least one unit dose of capecitabine; and (b) at least one unit dose of HKI-272.

In another aspect, a pharmaceutical composition is described and contains capecitabine, HKI-272, and at least one pharmaceutically acceptable carrier.

In still another aspect, a method of treating a neoplasm associated with overexpression or amplification of Erb-1 and/or Erb-2 in a mammal in need thereof is provided and includes administering a unit dose of a capecitabine compound and administering a unit dose of a HKI-272 compound.

In a separate aspect, a combination therapy for an Erb-1 overexpressing (amplified) and/or an Erb-2-overexpressing (amplified) neoplasm is provided. This combination therapy comprises a regimen involving the two anti-neoplastic agents SKI-606 (bosutinib) and capecitabine.

In another aspect, a combination therapy for treatment of a solid tumor neoplasm in a subject is provided which includes administering SKI-606 (Bosutinib) and administering capecitabine.

In still another aspect, a combination therapy is useful for treatment of breast cancer.

In yet another aspect, the combination therapy is utilized for treatment of ErbB-2 positive metastatic or locally advanced breast cancer is provided. This combination therapy comprises delivering a combination of SKI-606 and capecitabine.

In yet a further aspect, a pharmaceutical pack for treating a neoplasm in one individual mammal is provided and includes (a) at least one unit dose of capecitabine; and (b) at least one unit dose of SKI-606.

In another aspect, a pharmaceutical composition is described and contains capecitabine, SKI-606, and at least one pharmaceutically acceptable carrier.

In still another aspect, a method of treating a neoplasm associated with overexpression or amplification of Erb-1 and/or Erb-2 in a mammal in need thereof is provided and includes administering a unit dose of a capecitabine compound and administering a unit dose of a SKI-606 compound.

Other aspects and advantages of the invention will be readily apparent from the following detailed description of the invention.

DETAILED DESCRIPTION OF THE INVENTION

An anti-neoplastic regimen utilizing the two active components neratinib (HKI-272) and capecitabine are described. This regimen is particularly well suited for treatment of Erb-2 (HER-2)-associated neoplasms. In another embodiment, this regimen is used for the treatment of Erb-1-associated neoplasms. In one embodiment, these two components are the sole anti-neoplastic components in the regimen. In another embodiment, the regimen further involves delivery of other active agents, which are non-antineoplastic.

As used herein, "a HKI-272 compound" refers, in one embodiment, to a compound having the following core structure:

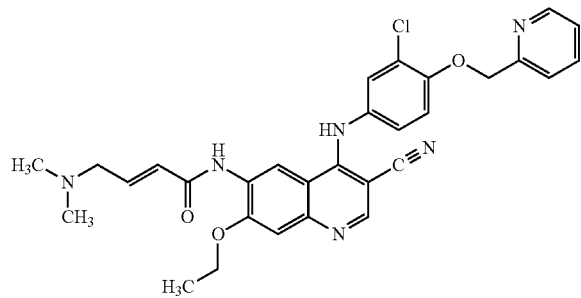 [SMILES: CCOc1cc2ncc(C#N)c(Nc3ccc(OCc4ccccn4)c(Cl)c3)c2cc1NC(=O)/C=C/CN(C)C]

or a derivative or pharmaceutically acceptable salt thereof. Suitable derivatives may include, e.g., an ester, ether, or carbamate. The core structure represented above is a particularly HKI-272 compound, called HKI-272 or neratinib, which has the chemical name [(2E)-N-[4-[[3-chloro-4-[(pyridin-2-yl)methoxy]phenyl]amino]-3-cyano-7-ethoxyquinolin-6-yl]-4-(dimethylamino)but-2-enamide]. In one embodiment, the HKI-272 compound useful in the compositions and methods described herein is HKI-272.

In another embodiment, an HKI-272 compound has the structure:

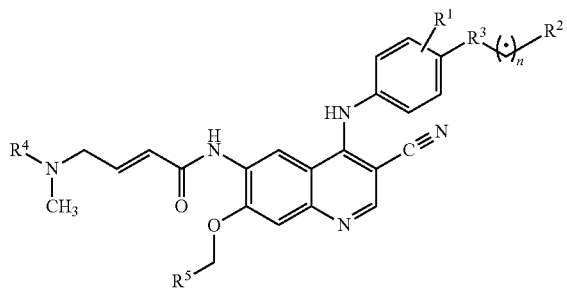

wherein:
$R^1$ is halogen;
$R^2$ is pyridinyl, thiophenyl, pyrimidinyl, thiazolyl, or phenyl, wherein $R^2$ is optionally substituted with up to three substituents;
$R^3$ is O or S;
$R^4$ is $CH_3$ or $CH_2CH_2OCH_3$;
$R^5$ is $CH_3$ or $CH_2CH_3$; and
n is 0 or 1.

The term "halogen" as used herein refers to Cl, Br, I, and F.

These HKI-272 compounds, of which HKI-272 is a species, are characterized by the ability to act as potent HER-2 inhibitors, as disclosed in U.S. Pat. Nos. 6,288,082 and 6,297,258 and U.S. Patent Application Publication No. 2007/0104721. These compounds and their preparation are described in detail in U.S. Patent Application Publication No. 2005/0059678. For convenience, "a HKI-272 compound" is used throughout this specification. However, in another embodiment, another compound of the structure(s) provided above is substituted for HKI-272 in one or more of the combinations described in detail below.

HKI-272, other HKI-272 compounds, and methods of making and formulating same have been described in, for example, U.S. Patent Application Publication No. 2005/0059678 and U.S. Pat. No. 6,002,008. The methods described in these documents can also be used to prepare the substituted 3-quinoline compounds used herein and are hereby incorporated by reference. In addition to the methods described in these documents, International Patent Publication Nos. WO-96/33978 and WO-96/33980, describe methods that are useful for the preparation of these HKI-272 compounds. Although these methods describe the preparation of certain quinazolines, they are also applicable to the preparation of correspondingly substituted 3-cyanoquinolines and are hereby incorporated by reference.

The chemical name for capecitabine is 5'-deoxy-5-fluoro-N-[(pentyloxy)-carbonyl]-cytidine. Capecitabine is covered in U.S. patents, including U.S. Pat. Nos. 4,966,891 and 5,472,949. Capecitabine is currently commercially available as XELODA® [ROCHE]. Methods for the manufacture of capecitabine are taught in U.S. Pat. Nos. 5,453,497 and 5,476,932. To the extent necessary, any and all of the foregoing patents and applications are used in accordance with the invention as disclosed.

The HKI-272 and capecitibine compounds and corresponding pharmaceutically acceptable salts or esters thereof include isomers either individually or as a mixture, such as enantiomers, diastereomers, and positional isomers.

An anti-neoplastic regimen utilizing the two active components bosutinib (SKI-606) and capecitabine are described. This regimen is particularly well suited for treatment of Erb-2 (HER-2)-associated neoplasms. In another embodiment, this regimen is used for the treatment of Erb-1-associated neoplasms. In one embodiment, these two components are the sole anti-neoplastic components in the regimen. In another embodiment, the regimen further involves delivery of other active agents, which are non-antineoplastic.

As used herein, SKI-606 refers, in one embodiment, to a Src inhibitor compound having the following core structure:

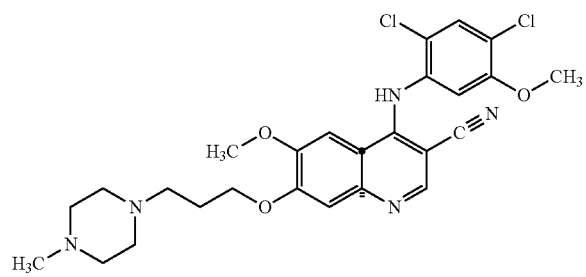

or a derivative or pharmaceutically acceptable salt thereof. Suitable derivatives may include, e.g., an ester, ether, or carbamate. The core structure represented above is called SKI-606 or bosutinib, which has the chemical name 4-(2,4-dichloro-5-methoxy-phenylamino)-6-methoxy7-[3-(4-methyl-piperizin-1-yl)-propoxy]-quinoline-3-carbonitrile). Other 4-anilino-3-cyanoquinolines are described in U.S. Pat. Nos. 6,002,008; 6,288,082; 6,297,258; 6,780,996; 7,297,795 and 7,399, 865.

The SKI-606 and capecitibine compounds and corresponding pharmaceutically acceptable salts or esters thereof include isomers either individually or as a mixture, such as enantiomers, diastereomers, and positional isomers.

"Pharmaceutically acceptable salts and esters" refers to salts and esters that are pharmaceutically acceptable and have the desired pharmacological properties. Such salts include, e.g., salts that can be formed where acidic protons present in the compounds are capable of reacting with inorganic or organic bases. Suitable inorganic salts include, e.g., those formed with the alkali metals or alkaline earth metals, e.g. sodium, potassium, magnesium, calcium, aluminum. Suitable organic salts also include, e.g., those formed with organic bases such as the amine bases, e.g., ethanolamine, diethanolamine, triethanolamine, tromethamine, N-methylglucamine, and the like, and those which can form N-tetraalkylammonium salts such as N-tetrabutylammonium salts. Pharmaceutically acceptable salts can also include acid addition salts formed from the reaction of basic moieties, such as amines, in the parent compound with inorganic acids (e.g., hydrochloric and hydrobromic acids) and organic acids (e.g., acetic acid, citric acid, maleic acid, propionic, lactic, tartaric, succinic, fumaric, maleic, malonic, mandelic, malic, phthalic, hydrochloric, hydrobromic, phosphoric, nitric, sulfuric, and the alkane- and arene-sulfonic acids such as methanesulfonic acid and benzenesulfonic acid naphthalenesulfonic, toluenesulfonic, camphorsulfonic). Other suitable examples of pharmaceutically acceptable salts include, but are not limited, to sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts.

Pharmaceutically acceptable esters include esters formed from carboxy, sulfonyloxy, and phosphonoxy groups present in the compounds of the invention, e.g., straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds utilized herein may be present in unsalified or unesterified form, or in salified and/or esterified form, and the naming of such compounds is intended to include both the original (unsalified and unesterified) compound and its pharmaceutically acceptable salts and esters. Also, one or more compounds utilized herein may be present in more than one stereoisomeric form, and the naming of such compounds is intended to include all single stereoisomers and all mixtures (whether racemic or otherwise) of such stereoisomers.

According to one embodiment, the use the combination HKI-272 and the capecitabine compound for the treatment of neoplasms is provided. In one embodiment, the neoplasm is an Erb-2 associated or overexpressing neoplasm. In one embodiment, the neoplasm is a breast cancer. For example, the breast cancer can be an Erb-2 positive metastatic breast cancer or a locally advanced breast cancer. In another embodiment, the neoplasm is an Erb-2 positive solid tumor.

According to a separate embodiment, the use the combination SKI-606 and the capecitabine compound for the treatment of neoplasms is provided. In one embodiment, the neoplasm is an Erb-2 associated or overexpressing neoplasm. In one embodiment, the neoplasm is a breast cancer. For example, the breast cancer can be an Erb-2 positive metastatic breast cancer or a locally advanced breast cancer. In another embodiment, the neoplasm is an Erb-2 positive solid tumor.

As used herein, the term "effective amount" or "pharmaceutically effective amount" when administered to a subject to treat a neoplasm, is sufficient to inhibit, slow, reduce, or eliminate lesions or tumor growth in a subject, or to inhibit, slow, or reduce progression of disease and/or to increase progression-free survival rate of the subject.

According to one embodiment, use of a combination of the HKI-272 compound and capecitabine compound also provides for the use of combinations in which the HKI compound and/or the capecitabine compound is used at a subtherapeutically effective dosage. A subtherapeutically effective dosage refers to a dose lower than the amount which is effective when the drug is delivered alone (monotherapy). Although less desirable, it is possible that one of the active agents may be used in a supratherapeutic amount, i.e., at a higher dosage in the combination than when used alone. In this embodiment, the other active agent(s) may be used in a therapeutic or subtherapeutic amount.

According to a separate embodiment, use of a combination of the SKI-606 compound and capecitabine compound also provides for the use of combinations in which the Src inhibitor compound and/or the capecitabine compound is used at a subtherapeutically effective dosage. A subtherapeutically effective dosage refers to a dose lower than the amount which is effective when the drug is delivered alone (monotherapy). Although less desirable, it is possible that one of the active agents may be used in a supratherapeutic amount, i.e., at a higher dosage in the combination than when used alone. In this embodiment, the other active agent(s) may be used in a therapeutic or subtherapeutic amount.

The term "treating" or "treatment" refers to the administration of the 4-anilino-3-cyanoquinoline compound (e.g. HKT-272, SKI-606, EKB-569) and capecitabine compounds to a subject to prevent or delay, to alleviate, or to arrest or inhibit development of the symptoms or conditions associated with neoplasms.

As used herein, neoplasms which amplify/overexpress erB-2 (used interchangeably with Her-2 and neu) include certain breast cancers. Other neoplasms in which erb-2 is amplified or overexpressed may include, ovarian, bladder, gastric, pancreatic, colorectal, prostate, and lung cancers, including non-small cell lung cancers.

Neoplasms in which ErbB1 is expressed or overexpressed include a variety of solid human tumors, including non-small cell lung (NSCL), prostate, breast, colorectal, and ovarian cancers. Methods for screening samples to determine if the neoplasm overexpresses erb-1 and/or erB-2/Her-2 are known to those of skill in the art.

As used herein, the term "providing" with respect to providing a 4-anilino-3-cyanoquinoline compound (e.g. HKI-272, SKI-606, EKB-569) and a capecitabine compound, means either directly administering said compound and a capecitabine compound, or administering a prodrug, derivative, or analog which will form an effective amount of said compound and/or capecitabine compound within the body.

As used herein and except where noted, the terms "individual", "subject" and "patient" are used interchangeably, and refer to any animal, including mammals, preferably mice, rats, other rodents, rabbits, dogs, cats, swine, cattle, sheep, horses, non-human primates, and humans. Desirably, the term "individual", "subject" or "patient" refers to a human. In most embodiments, the subjects or patients are in need of the therapeutic treatment. Accordingly, the term "subject" or "patient" as used herein means any mammalian patient or subject to which the 4-anilino-3-cyanoquinoline compound (e.g. HKI-272, SKI-606, EKB-569) and capecitabine compounds can be administered.

Regimen Using the HKI-272 Compound and Capecitabine Compound

As used herein, the components of the therapeutic combined regimen, i.e., the HKI-272 compound and the capecitabine compound, can be administered simultaneously. Alternatively, the two components can be administered in a staggered regimen, i.e., with the HKI-272 compound being given at a different time during the course of the cycle than the capecitabine compound. This time differential may range from several minutes, hours, days, weeks, or longer between administration of the at least two agents. Therefore, the term combination (or combined) does not necessarily mean administered at the same time or as a unitary dose or single composition, but that each of the components are administered during a desired treatment period. The agents may also be administered by different routes. In one embodiment, 1 "cycle" includes 21 days (3 weeks).

These regimens or cycles may be repeated, or alternated, as desired. Other dosage regimens and variations are foreseeable, and are determined through physician guidance.

In one embodiment, the capecitabine is administered at least once over a period of 21 days. More desirably, the capecitabine is administered daily for 14 days over a period of 21 days. Typically, a regimen involves repeating this dosage for 3 to 6 cycles.

In one embodiment, the capecitabine and/or HKI-272 compound is administered only once in the treatment. In another embodiment, the capecitabine and/or HKI-272 compound is administered at least once over a period of 21 days. In a further embodiment, the capecitabine and/or HKI-272 compound is administered at least twice over a period of 21 days. In still another embodiment, the capecitabine and/or HKI-272 compound is administered on days 1, 2, 3, 4, 5, 6, 7, 8, 9, 10, 11, 12, 13, 14, 15, 16, 17, 18, 19, 20, and/or 21 of the cycle.

In still a further embodiment, the capecitabine and/or HKI-272 compound is administered at least once daily. In yet another embodiment, the capecitabine and/or HKI-272 compound HKI-272 compound is administered on day 1. In still a further embodiment, the HKI-272 compound is administered orally at least once a day. In another embodiment, the HKI-272 compound is administered at least 1, 2, 3, or 4 times a day. In a further embodiment the capecitabine compound is administered 1, 2, 3 or 4 times a day.

In one embodiment, a single loading dose of the capecitabine compound and/or HKI-272 compound is administered. The single loading dose of the capecitabine compound and/or the HKI-272 compound may be the same dose as the subsequent doses or the single loading dose may be greater than the dose administered to the patient throughout the remaining treatment. In a further embodiment, the capecitabine compound/or the HKI-272 compound may be administered at a larger dose only once per cycle, i.e., one day per cycle.

Single doses and multiple doses of the HKI-272 and/or the capecitabine are contemplated. These compounds may be separately formulated in combination with one or more pharmaceutically acceptable carrier(s) and excipients.

Regimen Using the SKI-606 and Capecitabine

As used herein, the components of the therapeutic combined regimen, i.e., the SKI-606 compound and the capecitabine compound, can be administered simultaneously. Alternatively, the two components can be administered in a staggered regimen, i.e., with the SKI-606 compound being given at a different time during the course of the cycle than the capecitabine compound. This time differential may range from several minutes, hours, days, weeks, or longer between administration of the at least two agents. Therefore, the term combination (or combined) does not necessarily mean administered at the same time or as a unitary dose or single composition, but that each of the components are administered during a desired treatment period. The agents may also be administered by different routes. In one embodiment, 1 "cycle" includes 21 days (3 weeks).

These regimens or cycles may be repeated, or alternated, as desired. Other dosage regimens and variations are foreseeable, and are determined through physician guidance.

In one embodiment, the capecitabine is administered at least once over a period of 21 days. More desirably, the capecitabine is administered daily for 14 days over a period of 21 days. Typically, a regimen involves repeating this dosage for 3 to 6 cycles.

In one embodiment, the capecitabine and/or SKI-606 compound is administered only once in the treatment. In another embodiment, the capecitabine and/or SKI-606 compound is administered at least once over a period of 21 days. In a further embodiment, the capecitabine and/or SKI-606 compound is administered at least twice over a period of 21 days. In still another embodiment, the capecitabine and/or SKI-606 compound is administered on days 1, 2, 3, 4, 5, 6, 7, 8, 9, 10, 11, 12, 13, 14, 15, 16, 17, 18, 19, 20, and/or 21 of the cycle.

In still a further embodiment, the capecitabine and/or SKI-606 compound is administered at least once daily. In yet another embodiment, the capecitabine and/or SKI-606 compound SKI-606 compound is administered on day 1. In still a further embodiment, the SKI-606 compound is administered orally at least once a day. In another embodiment, the SKI-606 compound is administered at least 1, 2, 3, or 4 times a day. In a further embodiment the capecitabine compound is administered 1, 2, 3 or 4 times a day.

In one embodiment, a single loading dose of the capecitabine compound and/or SKI-606 compound is administered. The single loading dose of the capecitabine compound and/or the SKT-606 compound may be the same dose as the subsequent doses or the single loading dose may be greater than the dose administered to the patient throughout the remaining treatment. In a further embodiment, the capecitabine compound/or the SKI-606 compound may be administered at a larger dose only once per cycle, i.e., one day per cycle.

Single doses and multiple doses of the SKI-606 and/or the capecitabine are contemplated. These compounds may be separately formulated in combination with one or more pharmaceutically acceptable carrier(s) and excipients.

In one embodiment, suitable examples of pharmaceutical carriers used herein include, but are not limited to, excipients, diluents, fillers, disintegrants, lubricants and other agents that can function as a carrier. The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. Pharmaceutical compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable. Suitable pharmaceutically-acceptable excipients or carriers for a tablet or caplet formulation include, e.g., inert excipients such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl 4-hydroxybenzoate, and anti-oxidants, such as ascorbic acid. Tablet or caplet formulations may be uncoated or coated either to modify their disintegration and the subsequent absorption of the active ingredient within the gastrointestinal tract, or to improve their stability and/or appearance using conventional coating agents and procedures well known in the art.

According to one embodiment, the HKT-272 compound can be administered, e.g., orally, at a dose range of about 0.01 to 100 mg/kg. In one embodiment, the HKI-272 compound is administered at a dose range of about 0.1 to about 90 mg/kg. In another embodiment, the HKI-272 compound is administered at a dose range of about 1 to about 80 mg/kg. In a further embodiment, the HKI-272 compound is administered at a dose range of about 10 to about 70 mg/kg. In yet another embodiment, the HKI-272 compound is administered at a dose range of about 15 to about 60 mg/kg. In still a further embodiment, the HKI-272 compound is administered at a dose range of about 20 to about 240 mg per day, at least about 40 mg, at least about 120 mg, or at least about 160 mg, on the days in the cycle on which it is administered. One of skill in the art could routinely perform empirical activity tests to determine the bioactivity of the compound in bioassays and thus determine what dosage to administer when the compound is delivered by another route.

In one embodiment, the oral dosage of the HKI-272 compound is at least about 700 mg/week. In another embodiment, the oral dosage of the HKI-272 compound is about 800 mg/week to at least to about 1700 mg/week. In another embodiment, the oral dosage of the HKI-272 compound is about 840 mg/week to about 1680 mg/week. In another embodiment, the oral dosage of the HKI-272 compound is about 900 mg/week to about 1600 mg/week. In a further embodiment, the oral dosage of the HKI-272 compound is about 1000 mg/week to about 1500 mg/week. In yet another embodiment, the oral dosage of the HKI-272 compound is about 1100 mg/week to about 1400 mg/week. In still a further embodiment, the oral dosage of the HKI-272 compound is about 1200 mg/week to about 1300 mg/week. Precise dosages are determined by the administering physician based on experience with the individual subject to be treated. Other dosage regimens and variations are foreseeable, and are determined through physician guidance.

Capecitabine may be used according to the currently approved/recommended dose of capecitabine for monotherapy of colon or breast cancer, i.e., an amount equivalent to 1250 mg/m$^2$ administered orally twice daily (equivalent to 2500 mg/m$^2$ total daily dose) for 14 days followed by a 7-day rest period given as 3-week cycles, for as long as needed. Typically the mean duration of treatment is 3 to 6 three-week cycles. The currently approved unit dosage forms are a light peach-colored film coated tablet containing 150 mg of capecitabine and a peach-colored film coated tablet containing 500 mg of capecitabine. In another embodiment, the doses of capecitabine may be reduced for use in the combination therapy of the present invention. Alternatively, high doses of capecitabine may be used for a period of one to multiple days, with reduced doses being delivered on certain days within a cycle. For example, a daily starting oral dose may be in the range of, e.g., 1250 mg to 3000 mg, 1500 mg to 4000 mg, 1500 mg to 2000 mg, 2000 mg to about 3600 mg, or about 2400 mg to about 3600 mg per day, on the days in the cycle on which it is administered. In another embodiment, the combination of the invention permits lower daily doses (subtherapeutic) of the capecitabine to be used, thus minimizing the risk of dose-limiting side effects. In one embodiment, the daily dose of capecitabine is 750 mg to 2000 mg, 900 to 1800 mg, or about 1250 mg to 1450 mg/day.

Precise dosages are determined by the administering physician based on experience with the individual subject to be treated. Other dosage regimens and variations are foreseeable, and are determined through physician guidance. In one embodiment, the capecitabine compound is administered by i.v. infusion or orally, preferably in the form of tablets or capsules.

As described herein, subtherapeutically effective amounts of the HKI-272 compound and capecitabine compound may be used to achieve a therapeutic effect when administered in combination. In one embodiment, the HKI-272 compound is provided at dosages of 5 to 50% lower when provided along with the capecitabine compound. In another embodiment, the HKI-272 compound is provided at dosages of 10 to 25% lower when provided along with the capecitabine compound. In a further embodiment, the HKI-272 compound is provided at dosages of 15 to 20% lower when provided along with the capecitabine compound. In one embodiment, a resulting HKI-272 compound dosage is about 8 to 40 mg. In another embodiment, a resulting HKI-272 compound dosage is about 8 to 30 mg. In a further embodiment, a resulting HKI-272 compound dosage is about 8 to 25 mg. Subtherapeutically effective amounts of the HKI-272 compound and capecitabine compound are expected to reduce the side-effects of treatment.

The SKI-606 compound can be administered, e.g., orally, at a dose range of about 0.01 to 600 mg/kg. In one embodiment, the SKI-606 compound is administered at a dose range of about 0.1 to about 600 mg/kg. In another embodiment, the SKI-606 compound is administered at a dose range of about 1 to about 500 mg/kg. In a further embodiment, the SKI-606 compound is administered at a dose range of about 10 to about 500 mg/kg. In yet another embodiment, the SKI-606 compound is administered at a dose range of about 100 to about 600 mg/kg. In still a further embodiment, the SKI-606 compound is administered at a dose range of about 200 to about 400 mg per day, at least about 40 mg, at least about 120 mg, or at least about 160 mg, on the days in the cycle on which it is administered. One of skill in the art could routinely perform empirical activity tests to determine the bioactivity of the compound in bioassays and thus determine what dosage to administer when the compound is delivered by another route.

In one embodiment, the oral dosage of the SKI-606 compound is at least about 1000 mg/week. In another embodiment, the oral dosage of the SKI-606 compound is about 1000 mg/week to at least to about 3000 mg/week. In another embodiment, the oral dosage of the SKI-606 compound is about 800 mg/week to about 2800 mg/week. In another embodiment, the oral dosage of the SKI-606 compound is about 800 mg/week to about 2100 mg/week. In a further embodiment, the oral dosage of the SKI-606 compound is about 1000 mg/week to about 2500 mg/week. In yet another embodiment, the oral dosage of the SKI-606 compound is about 1100 mg/week to about 2400 mg/week. In still a further embodiment, the oral dosage of the SKI-606 compound is about 1200 mg/week to about 2800 mg/week. Precise dosages are determined by the administering physician based on experience with the individual subject to be treated. Other dosage regimens and variations are foreseeable, and are determined through physician guidance.

Capecitabine may be used according to the currently approved/recommended dose of capecitabine for monotherapy of colon or breast cancer, i.e., an amount equivalent to 250-500 mg/m$^2$ administered orally twice daily (equivalent to 500-1000 mg/m$^2$ total daily dose) for 14 days followed by a 7-day rest period given as 3-week cycles, for as long as needed. Typically the mean duration of treatment is 3 to 6 three-week cycles. The currently approved unit dosage forms are a light peach-colored film coated tablet containing 150 mg of capecitabine and a peach-colored film coated tablet containing 500 mg of capecitabine. In another embodiment, the doses of capecitabine may be reduced for use in the combination therapy of the present invention. Alternatively, high doses of capecitabine may be used for a period of one to multiple days, with reduced doses being delivered on certain days within a cycle. For example, a daily starting oral dose may be in the range of, e.g., 100 mg to 1500 mg, 250 mg to 1500 mg, 500 mg to 1000 mg, 500 mg to about 2000 mg, or about 500 mg to about 3600 mg per day, on the days in the cycle on which it is administered. In another embodiment, the combination of the invention permits lower daily doses (subtherapeutic) of the capecitabine to be used, thus minimizing the risk of dose-limiting side effects. In one embodiment, the daily dose of capecitabine is 500 mg to 1000 mg, 250 to 1500 mg, or about 100 mg to 2000 mg/day.

Alternatively, one or more of the active agents in the combination described herein is to be used in a supratherapeutic amount, i.e., at a higher dosage in the combination than when used alone. In this embodiment, the other active agent(s) are used in a therapeutic or subtherapeutic amount.

In one embodiment, a regimen as provided herein is used for treating a neoplasm characterized by an erB-2 (HER-2) overexpressing neoplasm. In another embodiment, a regimen as provided herein is used for treating a neoplasm characterized by overexpression of an erB-1 overexpressing neoplasm. In still another embodiment, a regimen as described herein is used for treating a breast cancer. In certain embodiments, the breast cancer may be an erB-2-overexpressing metastatic or locally advanced breast cancer.

In addition, the capecitabine compound/or 4-anilino-3-cyanoquinoline compound (e.g. HKI-272, SKI-606, EKB-569) may also be administered after completion of chemotherapy as maintenance therapy.

Optional Components of the Regimens

The regimens described herein may also include the administration of other active agents which are not anti-neoplastics, but which ameliorate the symptoms of the neoplastic disease and/or therapy.

In still further embodiment, the combination may include an anti diarrheal. One of skill in the art would readily be able to select a suitable antidiarrheal for use herein including, without limitation, loperamide or diphenoxylate hydrochloride and atropine sulfate. Alternatively, the anti-diarrheal may be administered to the patient prior to or subsequent to treatment with the capecitabine compound and/or the 4-anilino-3-cyanoquinoline compound (e.g. HKI-272, SKI-606, EKB-569).

In a further embodiment, the combination further contains an antiemetic agent. Examples of antiemetic agents include, without limitation, metoclopramide, Dolasetron, Granisetron, Ondansetron, Tropisetron, and Palonosetron, among others. Alternatively, the antiemetic may be administered to the patient prior to or subsequent to treatment with the capecitabine compound and/or the 4-anilino-3-cyanoquinoline compound (e.g. HKI-272, SKI-606, EKB-569).

In yet a further embodiment, the combination also contains an antihistamine. Examples of antihistamines include, without limitation, Cyclizine, Diphenhydramine, Dimenhydrinate (Gravol), Meclizine, Promethazine (Pentazine, Phenergan, Promacot), or Hydroxyzine, among others. Alternatively, the antihistamine may be administered to the patient prior to or subsequent to treatment with the capecitabine compound and/or HKI-272 compound.

In yet another embodiment, the combination may include a growth factor to prevent and/or treat neutropenia. Such growth factors may readily be selected by those skill in the art according to practice guidelines from the American Society of Clinical Oncology (ASCO; 2006). Alternatively, the growth factor may be administered to the patient prior to or subsequent to treatment with the capecitabine compound and/or the 4-anilino-3-cyanoquinoline compound (e.g. HKI-272, SKI-606, EKB-569).

In still another embodiment, the regimen may be used in combination with other anti-neoplastic agents.

As is typical with oncology treatments, dosage regimens are closely monitored by the treating physician, based on numerous factors including the severity of the disease, response to the disease, any treatment related toxicities, age, and health of the patient. Dosage regimens are expected to vary according to the route of administration.

The dosages and schedules described hereinbefore may be varied according to the particular disease state and the overall condition of the patient. For example, it may be necessary or desirable to reduce the above-mentioned doses of the components of the combination treatment in order to reduce toxicity. Dosages and schedules may also vary if, in addition to a combination of an 4-anilino-3-cyanoquinoline compound (e.g. HKI-272, SKI-606, EKB-569) and a capecitabine, one or more additional chemotherapeutic agents are used. Scheduling can be determined by the practitioner who is treating any particular patient using his professional skill and knowledge.

Pharmaceutical Packs and Kits

Also included is a product or pharmaceutical pack containing a course of an anti-neoplastic treatment for one individual mammal comprising one or more container(s) having one, one to four, or more unit(s) of the HKI-272 compound in unit dosage form and, optionally, one, one to four, or more unit(s) of the HKI-272 and capecitabine compounds, and optionally, another active agent. The combinations may be in the form of a kit of parts.

For the HKI-272 compound and/or capecitabine compound, it is desired each compound of the combination of compounds is in the form of a unit dose. The term "unit dose" or "unit dose form" as used herein describes a single dose form including, without limitation, tablets, caplets, capsules, powders in sachets or vials, saline infusion bags, as described above.

Unit dose forms contain from about 0.1 to about 300 mg of a HKI-272 compound. In another embodiment, the unit dose form contains about 5 to about 300 mg of the HKI-272 compound. In another embodiment, the unit dose form contains about 50 to about 300 mg of the HKI-272 compound. In a further embodiment, the unit dose form contains about 75 to about 300 mg of the HKI-272 compound. In still a further embodiment, the unit dose form contains about 100 to about 300 mg of the HKI-272 compound. In yet another embodiment, the unit dose form contains about 120 to about 300 mg of the HKI-272 compound. In yet a further embodiment, the unit dose form contains about 160 to about 300 mg of the HKI-272 compound. In another embodiment, the unit dose form contains about 200 to about 300 mg of the HKI-272 compound. In yet another embodiment, the unit dose form contains about 240 to about 300 mg of the HKI-272 compound. In a further embodiment, the unit dose form contains about at least about 120 mg. In still a further embodiment, the unit dose form contains at least about 160 mg. In another embodiment, the unit dose form contains at least about 240 mg.

Currently, unit doses of capecitabine are commercially available as 150 mg or 500 mg tablets under the mark XELODA®. However, other suitable unit doses may be prepared as desired or required.

The invention therefore includes administering an HKI-272 compound and capecitabine compound to a subject for the treatment of a neoplasm. In one embodiment, the HKI-272 compound is administered separately from the capecitabine compound. In a further embodiment, the HKI-272 compound is administered prior to the capecitabine compound. In another embodiment, the HKI-272 compound is administered subsequent to the capecitabine compound. In still another embodiment, the HKI-272 compound and the capecitabine compound are administered simultaneously, but separately. In one embodiment, the HKI-272 compound and the capecitabine compound are administered together as a combined preparation.

In one embodiment, a product contains an HKI-272 compound and capecitabine compound as a combined preparation for simultaneous, separate or sequential use in treating a neoplasm in a mammal in need thereof. In one embodiment, the HKI-272 compound is separately formulated from the capecitabine compound.

In one embodiment, a pharmaceutical pack contains a course of treatment of a neoplasm for one individual mammal, wherein the pack contains units of an HKI-272 compound in unit dosage form and units of a capecitabine compound in unit dosage form. In another embodiment, a pharmaceutical pack contains a course of treatment of a neoplasm for one individual mammal, wherein the pack contains units of an HKI-272 compound in unit dosage form and units of a capecitabine compound in unit dosage form. In yet another embodiment, a pharmaceutical pack as described herein contains a course of treatment of metastatic breast cancer for one individual mammal.

Also included is a product or pharmaceutical pack containing a course of an anti-neoplastic treatment for one individual mammal comprising one or more container(s) having one, one to four, or more unit(s) of the SKI-606 compound in unit dosage form and, optionally, one, one to four, or more unit(s) of the SKI-606 and capecitabine compounds, and optionally, another active agent. The combinations may be in the form of a kit of parts.

For the SKI-606 compound and/or capecitabine compound, it is desired each compound of the combination of compounds is in the form of a unit dose. The term "unit dose" or "unit dose form" as used herein describes a single dose form including, without limitation, tablets, caplets, capsules, powders in sachets or vials, saline infusion bags, as described above.

Unit dose forms contain from about 0.1 to about 600 mg of a SKI-606 compound. In another embodiment, the unit dose form contains about 5 to about 600 mg of the SKI-606 compound. In another embodiment, the unit dose form contains about 50 to about 500 mg of the SKI-606 compound. In a further embodiment, the unit dose form contains about 100 to about 500 mg of the SKI-606 compound. In still a further embodiment, the unit dose form contains about 150 to about 500 mg of the SKI-606 compound. In yet another embodiment, the unit dose form contains about 200 to about 400 mg of the SKI-606 compound. In a further embodiment, the unit dose form contains about at least about 120 mg. In still a further embodiment, the unit dose form contains at least about 160 mg. In another embodiment, the unit dose form contains at least about 200 mg.

Currently, unit doses of capecitabine are commercially available as 150 mg or 500 mg tablets under the mark XELODA®. However, other suitable unit doses may be prepared as desired or required.

The invention therefore includes administering an SKI-606 compound and capecitabine compound to a subject for the treatment of a neoplasm. In one embodiment, the SKI-606 compound is administered separately from the capecitabine compound. In a further embodiment, the SKI-606 compound is administered prior to the capecitabine compound. In another embodiment, the SKI-606 compound is administered subsequent to the capecitabine compound. In still another embodiment, the SKI-606 compound and the capecitabine compound are administered simultaneously, but separately. In one embodiment, the SKI-606 compound and the capecitabine compound are administered together as a combined preparation.

In one embodiment, a product contains an SKI-606 compound and capecitabine compound as a combined preparation for simultaneous, separate or sequential use in treating a neoplasm in a mammal in need thereof. In one embodiment, the SKI-606 compound is separately formulated from the capecitabine compound.

In one embodiment, a pharmaceutical pack contains a course of treatment of a neoplasm for one individual mammal, wherein the pack contains units of an SKI-606 compound in unit dosage form and units of a capecitabine compound in unit dosage form. In another embodiment, a pharmaceutical pack contains a course of treatment of a neoplasm for one individual mammal, wherein the pack contains units of an SKI-606 compound in unit dosage form and units of a capecitabine compound in unit dosage form. In yet another embodiment, a pharmaceutical pack as described herein contains a course of treatment of metastatic breast cancer for one individual mammal.

Administration of the individual components or a composition containing two or more of the individual components may employ any suitable route. Such routes may be selected from, e.g., oral, intravenous (i.v.), respiratory (e.g., nasal or intrabronchial), infusion, parenteral (aside from i.v., such as intralesional, intraperitoneal and subcutaneous injections), intraperitoneal, transdermal (including all administration across the surface of the body and the inner linings of bodily passages including epithelial and mucosal tissues), and vaginal (including intrauterine administration). Other routes of administration are also feasible and include, without limitation, liposome-mediated delivery, topical, nasal, sublingual, urethral, intrathecal, ocular or otic delivery, implant, rectal, or intranasal.

While the components may be delivered via the same route, a product or pack described herein may contain a capecitabine compound for delivery by a different route than that of an 4-anilino-3-cyanoquinoline compound (e.g. HKI-272, SKI-606, EKB-569) compound, e.g., one or more of the components may be delivered orally, while the other is administered by another route. In one embodiment, the 4-anilino-3-cyanoquinoline compound (e.g. HKI-272, SKI-606, EKB-569) is prepared for oral delivery and the capecitabine compound is prepared for intravenous delivery. Optionally, other active components may be delivered by the same or different routes as the 4-anilino-3-cyanoquinoline compound (e.g. HKI-272, SKI-606, EKB-569) and/or capecitabine compounds. Other variations would be apparent to one skilled in the art.

In still another embodiment, the compounds or components of the therapeutic regimen are administered once a week. In certain situations, dosing with the 4-anilino-3-cyanoquinoline compound (e.g. HKI-272, SKI-606, EKB-569) may be delayed or discontinued for a brief period (e.g., 1, 2 or three weeks) during the course of treatment. Such a delay or discontinuation may occur once, or more, during the course of treatment. The effective amount is known to one of skill in the art; it will also be dependent upon the form of the 4-anilino-3-cyanoquinoline compound (e.g. HKI-272, SKI-606, EKB-569). One of skill in the art could routinely perform empirical activity tests to determine the bioactivity of the 4-anilino-3-cyanoquinoline compound (e.g. HKI-272, SKI-606, EKB-569) in bioassays and thus determine a suitable dosage to administer.

The 4-anilino-3-cyanoquinoline compound (e.g. HKI-272, SKI-606, EKB-569) and capecitabine compounds or other optional compounds used in the combination and products described herein may be formulated in any suitable manner. However, the amounts of each compound in the unit dose can vary widely depending on the type of composition, regimen, size of a unit dosage, kind of excipients, and other factors well known to those of ordinary skill in the art. In one embodiment, the unit dose can contain, e.g., 0.000001 percent by weight (% w) to 10% w of either compound. In another embodiment the unit dose can contain about 0.00001% w to 1% w, with the remainder being the excipient or excipients.

The compositions described herein may be in a form suitable for oral administration, e.g., tablet, caplet, capsule, buccal forms, troches, lozenges and oral liquids, suspensions or solutions; parenteral injection (including intravenous, subcutaneous, intramuscular, intravascular or infusion), e.g., as a sterile solution, suspension or emulsion; topical administration, e.g., an ointment or cream; rectal administration, e.g., a suppository; or the route of administration may be by direct injection into the tumor or by regional delivery or by local delivery. In other embodiments, one or both components of the combination treatment may be delivered endoscopically, intratracheally, intralesionally, percutaneously, intravenously, subcutaneously, intraperitoneally or intratumorally. In general the compositions described herein may be prepared in a conventional manner using conventional excipients or carriers that are well known in the art. Pharmaceutical compositions for oral use may also be in the form of hard gelatin capsules in which the active ingredient is mixed with an inert solid excipient, e.g., calcium carbonate, calcium phosphate or kaolin, or as soft gelatin capsules in which the active ingredient is mixed with water or an oil, such as peanut oil, liquid paraffin or olive oil. In one embodiment, one or both of said capecitabine compound and said 4-anilino-3-cyanoquinoline compound (e.g. HKI-272, SKI-606, EKB-569) are delivered orally to said subject.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet or caplet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

Oral formulations herein, e.g., tablets, caplets, or capsules described above, may utilize standard delay or time release formulations to alter the absorption of the active compound(s). The oral formulation may also consist of administering the active ingredient in water or a fruit juice, containing appropriate solubilizers or emulsifiers as needed.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol and liquid polyethylene glycol), suitable mixtures thereof, and vegetable oils. Preferred injectable formulations containing capecitabine are described in the art. In one embodiment, the compounds may be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations may contain a preservative to prevent the growth of microorganisms. In one embodiment, one or both of the capecitabine and HKI-272 compounds are delivered intravenously.

For use herein, transdermal administrations include all administrations across the surface of the body and the inner linings of bodily passages including epithelial and mucosal tissues. Such administrations may be performed using the present compounds, or pharmaceutically acceptable salts thereof, in lotions, creams, foams, patches, suspensions, solutions, and suppositories (rectal and vaginal). Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

In another embodiment, one or both of the 4-anilino-3-cyanoquinoline compound (e.g. HKI-272, SKI-606, EKB-569) and capecitabine compounds can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of one or more compound into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). In other cases, the preferred preparation of one or more of the components can be a lyophilized powder.

Encapsulating materials can also be employed with one or more of the compounds and the term "composition" can include the active ingredient in combination with an encapsulating material as a formulation, with or without other carriers. For example, the compounds can also be delivered as microspheres for slow release in the body. In one embodiment, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao, *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months. Cachets can also be used in the delivery of the compounds of the present invention, e.g., anti-atherosclerotic medicaments.

In one embodiment a kit includes a first container with a suitable composition containing a HKI-272 compound and a second container with a suitable composition containing a capecitabine compound. Accordingly, there is provided a kit for use in the treatment or prophylaxis of cancer. This kit includes comprising: a) HKI-272 compound together with a pharmaceutically-acceptable excipient or carrier, in a first unit dosage form; b) a capecitabine compound together with a pharmaceutically-acceptable excipient or carrier, in a second unit dosage form; and c) a container for containing said first and second dosage forms.

In another embodiment, pharmaceutical packs contain a course of anti-neoplastic treatment for one individual mammal comprising a container having a unit of a HKI-272 compound in unit dosage form, a containing having a unit of a capecitabine compound, and optionally, a container with another active agent.

In a separate embodiment a kit includes a first container with a suitable composition containing a SKI-606 compound and a second container with a suitable composition containing a capecitabine compound. Accordingly, there is provided a kit for use in the treatment or prophylaxis of cancer. This kit includes comprising: a) SKI-606 compound together with a pharmaceutically-acceptable excipient or carrier, in a first unit dosage form; 1)) a capecitabine compound together with a pharmaceutically-acceptable excipient or carrier, in a second unit dosage form; and c) a container for containing said first and second dosage forms.

In some embodiments, the compositions are in packs in a form ready for administration. In other embodiments, the compositions are in concentrated form in packs, optionally with the diluent required to make a final solution for administration. In still other embodiments, the product contains a compound described herein in solid form and, optionally, a separate container with a suitable solvent or carrier.

In still other embodiments, the above packs/kits include other components, e.g., instructions for dilution, mixing and/or administration of the product, other containers, syringes, needles, etc. Other such pack/kit components are readily apparent to one of skill in the art.

In addition to the optional chemotherapeutic agents and optional compounds noted above, the regimens and methods described herein can be performed prior to, concurrently with, or subsequent to other non-medication procedures. In one embodiment, radiation may be performed prior to, concurrently with, or subsequent to treatment with the 4-anilino-3-cyanoquinoline compound (e.g. HKI-272, SKI-606, EKB-569) and capecitabine compounds.

In a further embodiment, a product containing capecitabine and a 4-anilino-3-cyanoquinoline compound (e.g. HKI-272, SKI-606, EKB-569) is provided. The product is useful as a combined preparation for simultaneous, separate or sequential use in treating a neoplasm in a mammal.

In still a further embodiment, a pharmaceutical pack for treating a neoplasm in one individual mammal is provided. The pharmaceutical pack contains at least one unit of capecitabine and at least one unit of a 4-anilino-3-cyanoquinoline compound (e.g. HKI-272, SKI-606, EKB-569).

In another embodiment, a pharmaceutical composition is provided and contains capecitabine, a 4-anilino-3-cyanoquinoline compound (e.g. HKI-272, SKI-606, EKB-569), and at least one pharmaceutically acceptable carrier. Desirably, the pharmaceutical composition is useful for treating a neoplasm in a mammal.

In still another embodiment, a method of treating a neoplasm associated with overexpression or amplification of HER-2 in a mammal in need thereof is provided. The method includes administering a unit dose of a capecitabine compound and administering a unit dose of a 4-anilino-3-cyanoquinoline compound (e.g. HKI-272, SKI-606, EKB-569). In one embodiment, to identify subject patients for treatment according to the methods of the invention, accepted screening methods are employed to determine risk factors associated with a targeted or suspected disease or condition or to determine the status of an existing disease or condition in a subject. These screening methods include, e.g., conventional workups to determine risk factors that are associated with the targeted or suspected disease or condition. These and other routine methods allow the clinician to select patients in need of therapy using the methods and formulations of the present invention. In one embodiment, the "individual", "subject" or "patient" may have had no previously chemotherapeutic treatment. In another embodiment, the "individual", "subject" or "patient" may have previously undergone chemotherapeutic treatment. In another embodiment, the "individual", "subject" or "patient" may have previously been administered an aniloquinazoline class inhibitor. In a further embodiment, the "individual", "subject" or "patient" may have previously been administered lapatinib or geftinib as the aniloquinazoline class inhibitor. Desirably, the blood count of the patient prior to treatment with the described combinations is stable enough to permit administration of the combinations described herein. In one embodiment, the neutrophil count of the patient prior to administration of the capecitabine and 4-anilino-3-cyanoquinoline (e.g. HKI-272, SKI-606, EKB-569) compounds is at least 1500. In another embodiment, the platelet count of the patient prior to administration of the capecitabine and 4-anilino-3-cyanoquinoline (e.g. HKI-272, SKI-606, EKB-569) compounds is at least 100,000/L.

The following examples illustrate of the uses of the combinations of the invention. It will be readily understood that alterations or modifications, e.g., in the formulation of the components, the routes of delivery, and the dosing, can be made for reasons known to those of skill in the art.

EXAMPLES

The combination of lapatinib and capecitabine has been chosen as the comparator therapy in this study due to recent approval by the FDA for the treatment of subjects with advanced or metastatic breast cancer whose tumors overexpress erbB-2 and who have received prior therapy including an anthracycline, a taxane, and trastuzumab. The registration trial indicated an ORR of 24% and median TTP of 27 weeks for the combination of both drugs (per independent review).

Preliminary pharmacokinetic (PK) analyses demonstrated that neratinib absorption was relatively slow, and the maximum concentration ($C_{max}$) was generally attained within 3 to 6 hours. After oral administration, the neratinib $C_{max}$ and area under the concentration-versus-time curve (AUC) increased in a dose-dependent manner in general. Mean steady-state $C_{max}$ and AUC values were 70.1 ng/mL and 975 ng·h/mL for the 180-mg dose group, respectively, 73.5 ng/mL and 939 ng·h/mL for the 240-mg dose group, respectively, 90.4 ng/mL and 1333 ng·h/mL for the 320-mg dose group, respectively, and 105 ng/mL and 1704 ng·h/mL for the highest dose of 400 mg, respectively. The neratinib exposure (AUC) increased 1.2- to 2.7-fold (mean accumulation ratio) when comparing the steady-state exposure on day 21 after repeated daily administration with the exposure on day 1 after administration of 80 to 400 mg of neratinib. The mean accumulation ratio was 1.2 after a 240-mg dose, indicating no significant accumulation of neratinib after repeated daily dose administration at the dose to be used in this proposed trial.

The data indicated a slow distribution of neratinib with a large apparent volume of distribution ($V_z/F$ on day 1: about 3188 to 6181 L) after oral absorption. After oral administration on day 1, neratinib was eliminated with a mean apparent terminal half-life ($t_{1/2}$) of approximately 13 to 17 hours. There was moderate to large variability in neratinib $t_{1/2}$, $C_{max}$, and AUC; coefficients of variation (CVs) generally ranged from 8% to 90%.

In an ongoing phase 2 study, neratinib is being administered as daily oral doses of 240 mg in subjects with erbB-2-overexpressing advanced or metastatic breast cancer, who received up to 4 prior cytotoxic chemotherapy treatment regimens, with prior trastuzumab therapy for metastatic or locally advanced disease (≥6 weeks) or with no prior exposure to erbB-2-targeted treatment. Preliminary results were obtained for 124 subjects evaluable for efficacy based on independent assessment and 131 subjects evaluable per investigator assessment. For subjects with prior trastuzumab containing therapy in the metastatic setting, the ORR was 26% (95% CI: 16-39%; independently assessed) and 35% (95% CI: 23-47%; investigator assessed), while an ORR of 51% (95% CI: 38-64%; independently assessed) and 62% (95% CI: 49-74%; investigator assessed) was observed in trastuzumab naïve subjects. Median Progression Free Survival (PFS) for independent (and investigator) assessment was 23 (22), with a 16-week PFS rate of 61% (57%) in subjects who had received prior trastuzumab. For trastuzumab naïve subjects, PFS per independent (and investigator) assessment was 40 (35), with a 16-week PFS rate of 75% (78%).

The predominant AE was diarrhea, which was reversible and generally manageable by medication, temporary discontinuation of treatment, or dose reduction. Diarrhea that was considered related to neratinib occurred with a frequency of 94% of the subjects. Of those, grade 3-4 diarrhea was experienced by 25% of the subjects. Other common AEs were nausea (related to neratinib in 30%, grade 3-4 in 2% of the subjects), vomiting (related in 23%, grade 3-4 in 2%), fatigue (related in 20%, grade 3-4 in <2%), and anorexia (related in 16%, grade 3-4 in 4%). These data show that daily oral doses of 240 mg of neratinib are generally well tolerated, and neratinib has significant antitumor activity in subjects with erbB-2-positive advanced breast cancer [Burstein, H J, Awada A, Badwe R, et al. 2007. Presented at the Poster presented at the SABCS, San Antonio, USA].

Example 1

Anti-tumor Activity of Neratinib (HKI-272) and Capecitabine Combination

Subjects with solid tumors will be enrolled in each dose group of the combination of neratinib and capecitabine. Each subject will participate in only 1 dose group. For the purpose of this study, a cycle is defined as a 21-day period.

Each subject will participate at only 1 dose level. Subjects will receive oral neratinib tablets (160 or 240 mg) daily in combination with oral capecitabine (750 or 1000 mg/m² BID (twice daily)) on days 1-14 of a 21-day cycle (no capecitabine administered days 15-21). For comparative purposes, lapatinib [TYKERB®] is administered orally once daily continuously according to manufacture's instruction.

| Dose level | Neratinib dose (mg) Continuous daily oral dosing | Capecitabine dose (mg/m$^2$) BID Days 1-14 of each 21-day cycle |
|---|---|---|
| 1 | 160 | 750 (total 1500 daily) |
| 2 | 240 | 750 (total 1500 daily) |
| 3 | 240 | 1000 (total 2000 daily) |

If dose level 1 is not tolerated, Part 2 will proceed with 2 arms: A (neratinib) and C (lapatinib + capecitabine).
If dose level 1 is tolerated but dose level 2 is not tolerated, an intermediate dose level at 200 mg of neratinib in combination with 750 mg/m$^2$ BID capecitabine may be investigated for MTD.
Dose delays and adjustments will be permitted. All subjects are allowed a maximum of 3 consecutive weeks dose delay to allow for toxicities to resolve.

As used herein, a complete response (CR) refers to the disappearance of all target lesions. A partial response (PR) refers to an at least 30% decrease in the sum of the longest diameter (LD), taking as reference the baseline sum LD. Stable disease is defined as having neither sufficient shrinkage to qualify for PR nor sufficient increase to qualify for PD, taking as reference the smallest sum LD since treatment started.

Example 2

HKI-272+Capecitabine in erbB-2 Positive Breast Cancer

Patients having diagnosed metastatic breast cancers are treated using a regimen of HKI-272 and capecitabine for three 21-day cycles. Control groups include patients who will receive oral HKI-272 monotherapy (240 mg daily) (Group 1) or a combination of lapatinib [TYKERB®, oral 1250 mg daily] and capecitabine [XELODA®, oral 2000 mg daily] (Group 2) according to manufacturer recommendations.

Patients receive oral HKI-272 tablets (either 160 mg or 240 mg) daily in combination with oral capecitabine (either 750 mg or 1000 mg twice daily) on days 1-14 of a 21-day cycle (no capecitabine administered days 15-21). Oral dosing of HKI-272 begins at cycle 1 and continues on the remaining days of the each cycle.

It is anticipated that results will show that HKI-272 in combination with capecitabine will significantly improve objective response rate as compared to the combination of lapatinib and capecitabine and/or prolonged subject's time to tumor progression (TTP) when compared to capecitabine monotherapy. It is further anticipated that side effects will be minimized as compared to the combination of lapatinib and capecitabine, in view of the lower effective dosages permitted by the combination of HKI-272 and capecitabine.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

Example 3

Anti-tumor Activity of Bosutinib (SKI-606) and Capecitabine Combination

Subjects with solid tumors will be enrolled in each dose group of the combination of bosutinib and capecitabine. Each subject will participate in only 1 dose group. For the purpose of this study, a cycle is defined as a 21-day period.

Each subject will participate at only 1 dose level. Subjects will receive oral bosutinib tablets (200-400 mg) daily in combination with oral capecitabine (500-1000 mg/m$^2$ BID (twice daily)) on days 1-14 of a 21-day cycle (no capecitabine administered days 15-21). For comparative purposes, lapatinib [TYKERB®] is administered orally once daily continuously according to manufacture's instruction.

| Dose level | Bosutinib dose (mg) Continuous daily oral dosing | Capecitabine dose (mg/m$^2$) BID Days 1-14 of each 21-day cycle |
|---|---|---|
| 1 | 200 | 250 (total 500 daily) |
| 2 | 300 | 300 (total 600 daily) |
| 3 | 400 | 500 (total 1000 daily) |

If dose level 1 is not tolerated, Part 2 will proceed with 2 arms: A (bosutinib) and C (lapatinib + capecitabine).
If dose level 1 is tolerated but dose level 2 is not tolerated, an intermediate dose level at 200 mg of bosutinib in combination with 750 mg/m$^2$ BID capecitabine may be investigated for MTD.
Dose delays and adjustments will be permitted. All subjects are allowed a maximum of 3 consecutive weeks dose delay to allow for toxicities to resolve.

As used herein, a complete response (CR) refers to the disappearance of all target lesions. A partial response (PR) refers to an at least 30% decrease in the sum of the longest diameter (LD), taking as reference the baseline sum LD. Stable disease is defined as having neither sufficient shrinkage to qualify for PR nor sufficient increase to qualify for PD, taking as reference the smallest sum LD since treatment started.

Example 4

SKI-606+Capecitabine in erbB-2 Positive Breast Cancer

Patients having diagnosed metastatic breast cancers are treated using a regimen of SKI-606 and capecitabine for three 21-day cycles. Control groups include patients who will receive oral SKI-606 monotherapy (200-400 mg daily) (Group 1) or a combination of lapatinib [TYKERB®, oral 1250 mg daily] and capecitabine [XELODA®, oral 1000 mg daily] (Group 2) according to manufacturer recommendations.

Patients receive oral SKI-600 tablets (either 200 mg or 400 mg) daily in combination with oral capecitabine (either 250 mg or 500 mg twice daily) on days 1-14 of a 21-day cycle (no capecitabine administered days 15-21). Oral dosing of SKI-606 begins at cycle 1 and continues on the remaining days of the each cycle.

It is anticipated that results will show that SKI-606 in combination with capecitabine will significantly improve objective response rate as compared to the combination of lapatinib and capecitabine and/or prolonged subject's time to tumor progression (TTP) when compared to capecitabine monotherapy. It is further anticipated that side effects will be minimized as compared to the combination of lapatinib and capecitabine, in view of the lower effective dosages permitted by the combination of SKI-606 and capecitabine.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A method for treating an ErbB-2 positive metastatic breast cancer in a subject; comprising administering to the subject neratinib and capecitabine.

2. The method according to claim 1, wherein the breast cancer is a locally advanced breast cancer.

3. The method according to claim 1, wherein one or both of capecitabine and neratinib is administered in a subtherapeutically effective amount.

4. The method according to claim 1, wherein neratinib and capecitabine are administered orally.

5. The method according to claim 1, wherein neratinib and capecitabine are administered concurrently, sequentially, or simultaneously.

6. The method according to claim 1, wherein neratinib is administered in a unit dose.

7. The method according to claim 1, wherein capecitabine is administered in a unit dose.

8. The method according to claim 1, wherein capecitabine is administered in an amount of about 1250 mg to about 3000 mg daily.

9. The method according to claim 1, wherein capecitabine is administered at least once over a period of 21 days.

10. The method according to claim 1, wherein the administration of capecitabine is continued for 3 to 6 cycles.

11. The method according to claim 10, wherein 1 cycle comprises 21 days.

12. The method according to claim 1, wherein neratinib is administered in an amount of at least 40 mg per day.

13. The method according to claim 11, wherein neratinib is administered in an amount of at least 120 mg per day.

14. The method according to claim 12, wherein neratinib is administered in an amount of at least 240 mg per day.

15. The method according to claim 1, wherein neratinib is administered daily.

16. The method according to claim 1, wherein neratinib is administered at least once daily.

17. The method according to claim 1, wherein neratinib is administered for at least 2 continuous weeks.

18. The method according to claim 1, wherein neratinib is administered in an amount of at least 240 mg per day continuously and capecitabine is administered in an amount of at least 1500 mg per day on days 1 and 14 of each 21-day cycle.

19. The method according to claim 1, wherein neratinib is administered before capecitabine.

20. The method according to claim 1, wherein neratinib is administered after capecitabine.

21. The method according to claim 1, wherein neratinib and capecitabine are administered simultaneously.

22. The method according to claim 1, wherein administration of capecitabine is discontinued after about 24 weeks.

23. A method for treating an ErbB-2 positive metastatic breast cancer in a subject, wherein one treatment cycle comprises 21 days, comprising:
    (a) orally administering to the subject at least one unit dose of neratinib daily starting on day 1 of said cycle; and
    (b) orally administering to the subject at least one unit dose of capecitabine on days 1 to 14 of said cycle.

* * * * *